(12) United States Patent
Heronen et al.

(10) Patent No.: US 12,090,079 B2
(45) Date of Patent: Sep. 17, 2024

(54) THORACIC LUMBAR SACRAL ORTHOSIS ATTACHMENT

(71) Applicant: OSSUR ICELAND EHF, Reykjavik (IS)

(72) Inventors: Nathan Heronen, Foothill Ranch, CA (US); Jane Price, Foothill Ranch, CA (US); Harry Duane Romo, Foothill Ranch, CA (US)

(73) Assignee: OSSUR ICELAND EHF, Reykjavik (IS)

( * ) Notice: Subject to any disclaimer, the term of this patent is extended or adjusted under 35 U.S.C. 154(b) by 0 days.

(21) Appl. No.: 18/315,024

(22) Filed: May 10, 2023

(65) Prior Publication Data
US 2023/0277354 A1    Sep. 7, 2023

Related U.S. Application Data

(63) Continuation of application No. 17/451,927, filed on Oct. 22, 2021, now Pat. No. 11,684,506, which is a
(Continued)

(51) Int. Cl.
*A61F 5/02* (2006.01)
*A61F 5/03* (2006.01)

(52) U.S. Cl.
CPC ............ *A61F 5/028* (2013.01); *A61F 5/022* (2013.01); *A61F 5/024* (2013.01); *A61F 5/026* (2013.01); *A61F 5/03* (2013.01)

(58) Field of Classification Search
CPC ........ A61F 5/02–03; A61F 5/04–05883; A61F 5/30–34; A41D 13/05;
(Continued)

(56) References Cited

U.S. PATENT DOCUMENTS

| 7,916 | A | 1/1851 | Knapp |
| 61,487 | A | 1/1867 | Vollschwitz |

(Continued)

FOREIGN PATENT DOCUMENTS

| AU | 2010271020 A2 | 2/2012 |
| AU | 2010286851 A2 | 5/2012 |

(Continued)

OTHER PUBLICATIONS

Bledsoe Products, "Philippon K.A.F. Positioning Kit". Http://bledsoebrace.com/products/kaf.asp [retrieved from the internet May 10, 2012].
(Continued)

*Primary Examiner* — Michelle J Lee
(74) *Attorney, Agent, or Firm* — Workman Nydegger; Justin J. Cassell

(57) ABSTRACT

A thoracic lumbar sacral orthosis attachment for configuring an orthopedic device as a thoracic lumbar sacral orthosis by connecting the attachment to the orthopedic device. The attachment has an anterior aspect including an anterior panel arranged to connect to an orthopedic device. An anterior thoracic extension (ATE) is securable to the anterior panel, and a support bar extends from the ATE. A strap system includes an axillary strap system and/or a shoulder strap system removably securing onto a surface of the orthopedic device, and/or the ATE.

17 Claims, 17 Drawing Sheets

Related U.S. Application Data continuation of application No. 16/124,921, filed on Sep. 7, 2018, now Pat. No. 11,246,734.

(60) Provisional application No. 62/555,482, filed on Sep. 7, 2017.

(58) Field of Classification Search
CPC ........ A41D 13/0518–0531; A45F 3/10; A63B 71/08; A63B 71/12; A63B 71/1291; A63B 2071/1208
See application file for complete search history.

(56) References Cited

U.S. PATENT DOCUMENTS

| | | |
|---|---|---|
| 181,948 A | 9/1876 | Kleinschuster |
| 232,420 A | 9/1880 | Smith |
| 321,145 A | 6/1885 | Spencer |
| 321,146 A | 6/1885 | Spencer |
| 328,638 A | 10/1885 | Battershall |
| 368,699 A | 8/1887 | Zervas |
| 386,642 A | 7/1888 | Mann |
| 507,172 A | 10/1893 | Shelden |
| 571,749 A | 11/1896 | Colton |
| 596,849 A | 1/1898 | Combler |
| 601,446 A | 3/1898 | Mestler |
| 616,196 A | 12/1898 | Medbury |
| 629,900 A | 8/1899 | Fosburgh |
| 639,072 A | 12/1899 | Lyons |
| 664,250 A | 12/1900 | Fitzpatrick |
| 709,055 A | 9/1902 | Sheldon |
| 787,894 A | 9/1902 | Sheldon |
| 714,124 A | 11/1902 | Adams |
| 746,563 A | 12/1903 | McMahon |
| 772,926 A | 10/1904 | Colton |
| 888,490 A | 5/1908 | Haas |
| 894,066 A | 7/1908 | Carpa |
| 980,457 A | 1/1911 | Toles |
| 1,124,595 A | 1/1915 | Dailey et al. |
| 1,124,596 A | 1/1915 | Dalpe |
| 1,316,915 A | 9/1919 | Meyer et al. |
| 1,393,188 A | 10/1921 | Whiteman |
| 1,431,903 A | 10/1922 | Becker |
| 1,463,579 A | 7/1923 | Funck |
| 1,469,661 A | 10/1923 | Migita |
| 1,481,903 A | 1/1924 | Hart |
| 1,530,713 A | 3/1925 | Clark |
| 1,558,661 A | 10/1925 | Yeganian |
| 1,607,032 A | 11/1926 | Whitley |
| 1,755,641 A | 4/1930 | Foulke |
| 1,948,785 A | 2/1934 | Dondelinger |
| 1,981,157 A | 11/1934 | Walter |
| 2,036,484 A | 4/1936 | Le May |
| 2,100,964 A | 11/1937 | Kendrick |
| 2,117,309 A | 5/1938 | Fritsch |
| 2,219,475 A | 10/1940 | Flaherty |
| 2,409,381 A | 10/1946 | Pease, Jr. |
| 2,543,370 A | 2/1951 | Jonathan et al. |
| 2,554,337 A | 5/1951 | Lampert |
| 2,630,801 A | 3/1953 | Mest et al. |
| 2,696,011 A | 12/1954 | Galdik |
| 2,749,550 A | 6/1956 | Pease |
| 2,775,767 A | 1/1957 | Gould |
| 2,793,368 A | 5/1957 | Nouel |
| 2,808,050 A | 10/1957 | Ward |
| 2,815,021 A | 12/1957 | Freeman |
| 2,828,737 A | 4/1958 | Hale |
| 2,904,040 A | 9/1959 | Hale |
| 2,906,260 A | 9/1959 | Myers |
| 2,906,261 A | 9/1959 | Craig |
| 3,095,875 A | 7/1963 | Ian et al. |
| 3,096,760 A | 7/1963 | Nelkin |
| 3,128,514 A | 4/1964 | Kenneth et al. |
| 3,274,996 A | 9/1966 | Jewett |
| 3,282,264 A | 11/1966 | Connelly |
| 3,351,053 A | 11/1967 | Stuttle |
| 3,371,351 A | 3/1968 | Allain |
| 3,434,469 A | 3/1969 | Swift |
| 3,480,012 A | 11/1969 | Smithers et al. |
| 3,509,875 A | 5/1970 | Richter |
| 3,548,817 A | 12/1970 | Mittasch |
| 3,563,431 A | 2/1971 | Pletz |
| 3,570,480 A | 3/1971 | Stubbs |
| 3,578,773 A | 5/1971 | Schultz |
| 3,600,717 A | 8/1971 | McKeehan |
| 3,601,819 A | 8/1971 | Herrmann |
| 3,603,316 A | 9/1971 | Lehman |
| 3,762,421 A | 10/1973 | Sax |
| 3,771,513 A | 11/1973 | Velazquez |
| 3,793,749 A | 2/1974 | Gertsch et al. |
| 3,808,644 A | 5/1974 | Schoch |
| 3,812,850 A | 5/1974 | Reiman |
| 3,816,211 A | 6/1974 | Haigh |
| 3,834,048 A | 9/1974 | Maurer |
| 3,889,664 A | 6/1975 | Heuser et al. |
| 3,902,503 A | 9/1975 | Gaylord, Jr. |
| 3,920,008 A | 11/1975 | Lehman |
| 3,926,182 A | 12/1975 | Stabholz |
| 3,927,665 A | 12/1975 | Wax |
| 3,945,376 A | 3/1976 | Kuehnegger |
| 4,042,433 A | 8/1977 | Hardy et al. |
| 4,055,168 A | 10/1977 | Miller et al. |
| 4,071,387 A | 1/1978 | Schlaepfer |
| 4,099,524 A | 7/1978 | Cueman et al. |
| 4,114,788 A | 9/1978 | Zufich |
| 4,162,672 A | 7/1979 | Yazaki |
| 4,173,973 A | 11/1979 | Hendricks |
| 4,175,553 A | 11/1979 | Rosenberg |
| 4,182,338 A | 1/1980 | Stanulis |
| 4,230,101 A | 10/1980 | Gold |
| 4,261,081 A | 4/1981 | Lott |
| 4,285,336 A | 8/1981 | Oebser et al. |
| 4,308,861 A | 1/1982 | Kelly |
| 4,322,092 A | 3/1982 | Feucht et al. |
| 4,383,523 A | 5/1983 | Schurman |
| 4,392,489 A | 7/1983 | Wagner, Sr. |
| 4,433,456 A | 2/1984 | Baggio |
| RE31,564 E | 4/1984 | Hendricks |
| 4,475,543 A | 10/1984 | Brooks et al. |
| 4,479,495 A | 10/1984 | Isaacson |
| 4,494,536 A | 1/1985 | Latenser |
| 4,502,471 A | 3/1985 | Owens |
| 4,508,110 A | 4/1985 | Modglin |
| 4,531,515 A | 7/1985 | Rolfes |
| 4,555,830 A | 12/1985 | Petrini et al. |
| 4,559,933 A | 12/1985 | Batard et al. |
| 4,569,336 A | 2/1986 | Wheeler |
| 4,574,500 A | 3/1986 | Aldinio et al. |
| 4,574,789 A | 3/1986 | Forster |
| 4,574,790 A | 3/1986 | Wellershaus |
| 4,590,939 A | 5/1986 | Sakowski |
| 4,608,971 A | 9/1986 | Borschneck |
| 4,616,524 A | 10/1986 | Bidoia |
| 4,619,657 A | 10/1986 | Keates et al. |
| 4,628,913 A | 12/1986 | Lerman |
| 4,631,839 A | 12/1986 | Bonetti et al. |
| 4,631,840 A | 12/1986 | Gamm |
| 4,635,626 A | 1/1987 | Lerman |
| 4,640,269 A | 2/1987 | Goins |
| 4,648,390 A | 3/1987 | Friddle |
| 4,649,574 A | 3/1987 | Michels |
| 4,654,985 A | 4/1987 | Chalmers |
| 4,655,201 A | 4/1987 | Pirmantgen |
| 4,658,807 A | 4/1987 | Swain |
| 4,660,302 A | 4/1987 | Arieh et al. |
| 4,677,699 A | 7/1987 | Barabe |
| 4,677,969 A | 7/1987 | Calabrese |
| 4,680,878 A | 7/1987 | Pozzobon et al. |
| 4,691,696 A | 9/1987 | Farfan de los Godos |
| 4,696,291 A | 9/1987 | Tyo |
| 4,697,583 A | 10/1987 | Mason et al. |
| 4,697,592 A | 10/1987 | Maddux et al. |
| 4,716,898 A | 1/1988 | Chauve et al. |
| 4,719,670 A | 1/1988 | Kurt |

(56) References Cited

U.S. PATENT DOCUMENTS

| | | |
|---|---|---|
| 4,719,709 A | 1/1988 | Vaccari |
| 4,761,834 A | 8/1988 | Kolb |
| 4,796,610 A | 1/1989 | Cromartie |
| 4,799,297 A | 1/1989 | Baggio et al. |
| 4,802,291 A | 2/1989 | Sartor |
| 4,805,605 A | 2/1989 | Glassman |
| 4,807,605 A | 2/1989 | Mattingly |
| 4,811,503 A | 3/1989 | Iwama |
| 4,843,688 A | 7/1989 | Ikeda |
| 4,862,878 A | 9/1989 | Davison et al. |
| 4,870,761 A | 10/1989 | Tracy |
| 4,905,678 A | 3/1990 | Cumins et al. |
| 4,923,474 A | 5/1990 | Klasson et al. |
| 4,937,952 A | 7/1990 | Olivieri |
| 4,961,544 A | 10/1990 | Bidoia |
| 4,963,208 A | 10/1990 | Muncy et al. |
| 4,976,257 A | 12/1990 | Akin et al. |
| 4,986,263 A | 1/1991 | Dickerson et al. |
| 4,997,438 A | 3/1991 | Nipper |
| 5,027,482 A | 7/1991 | Torppey |
| 5,072,725 A | 12/1991 | Miller |
| 5,074,288 A | 12/1991 | Miller |
| 5,092,321 A | 3/1992 | Spademan |
| 5,098,770 A | 3/1992 | Paire |
| 5,105,828 A | 4/1992 | Grant |
| 5,111,807 A | 5/1992 | Spahn et al. |
| 5,117,567 A | 6/1992 | Berger |
| 5,120,288 A | 6/1992 | Sinaki |
| 5,121,741 A | 6/1992 | Bremer et al. |
| 5,127,897 A | 7/1992 | Roller |
| 5,135,470 A | 8/1992 | Reeves |
| 5,135,471 A | 8/1992 | Houswerth |
| 5,154,690 A | 10/1992 | Shiono |
| 5,157,813 A | 10/1992 | Carroll |
| 5,170,505 A | 12/1992 | Rohrer |
| 5,171,296 A | 12/1992 | Herman |
| 5,176,131 A | 1/1993 | Votel et al. |
| 5,177,882 A | 1/1993 | Berger |
| 5,181,331 A | 1/1993 | Berger |
| 5,183,036 A | 2/1993 | Spademan |
| D334,063 S | 3/1993 | Dewall et al. |
| 5,199,940 A | 4/1993 | Morris et al. |
| 5,201,074 A | 4/1993 | Dicker |
| 5,203,765 A | 4/1993 | Friddle, Jr. |
| 5,215,518 A | 6/1993 | Rosen |
| 5,226,874 A | 7/1993 | Heinz et al. |
| 5,230,698 A | 7/1993 | Garth |
| 5,259,831 A | 11/1993 | Lebron |
| 5,259,833 A | 11/1993 | Barnett |
| 5,267,928 A | 12/1993 | Barile et al. |
| 5,295,947 A | 3/1994 | Muncy |
| 5,295,996 A | 3/1994 | Blair |
| 5,307,521 A | 5/1994 | Davis |
| 5,313,952 A | 5/1994 | Hoch |
| 5,318,575 A | 6/1994 | Chesterfield et al. |
| 5,327,662 A | 7/1994 | Hallenbeck |
| 5,334,135 A | 8/1994 | Grim et al. |
| 5,342,289 A | 8/1994 | Munny |
| 5,346,461 A | 9/1994 | Heinz et al. |
| 5,363,863 A | 11/1994 | Lelli et al. |
| 5,365,947 A | 11/1994 | Bonutti |
| 5,368,552 A | 11/1994 | Williamson et al. |
| 5,376,129 A | 12/1994 | Faulkner et al. |
| 5,383,893 A | 1/1995 | Daneshvar |
| 5,387,245 A | 2/1995 | Fay et al. |
| 5,399,151 A | 3/1995 | Smith |
| 5,421,809 A | 6/1995 | Rise |
| 5,423,852 A | 6/1995 | Daneshvar |
| 5,429,587 A | 7/1995 | Gates |
| 5,433,648 A | 7/1995 | Frydman |
| 5,433,697 A | 7/1995 | Cox |
| 5,435,015 A | 7/1995 | Ellis-Brewer |
| 5,437,614 A | 8/1995 | Grim |
| 5,437,617 A | 8/1995 | Heinz et al. |
| 5,437,619 A | 8/1995 | Malewicz et al. |
| 5,449,338 A | 9/1995 | Trudell |
| 5,450,858 A | 9/1995 | Zablotsky et al. |
| 5,466,214 A | 11/1995 | Calderon-Garciduenas |
| 5,484,395 A | 1/1996 | Deroche |
| 5,499,965 A | 3/1996 | Sanchez |
| 5,500,959 A | 3/1996 | Yewer, Jr. |
| 5,502,902 A | 4/1996 | Sussmann |
| 5,503,314 A | 4/1996 | Fiscus |
| 5,503,620 A | 4/1996 | Danzger |
| 5,507,681 A | 4/1996 | Smith et al. |
| 5,507,834 A | 4/1996 | Laghi |
| 5,520,619 A | 5/1996 | Martin |
| 5,522,792 A | 6/1996 | Bassett et al. |
| 5,531,669 A | 7/1996 | Varnau |
| 5,536,246 A | 7/1996 | Saunders |
| 5,539,020 A | 7/1996 | Bracken et al. |
| 5,548,843 A | 8/1996 | Chase et al. |
| 5,551,950 A | 9/1996 | Oppen |
| 5,556,374 A | 9/1996 | Grace et al. |
| 5,558,628 A | 9/1996 | Bzoch |
| 5,569,171 A | 10/1996 | Muncy |
| 5,571,355 A | 11/1996 | Kornylo |
| 5,599,287 A | 2/1997 | Beczak et al. |
| 5,599,288 A | 2/1997 | Shirley et al. |
| 5,603,122 A | 2/1997 | Kania |
| 5,620,412 A | 4/1997 | Modglin |
| 5,622,529 A | 4/1997 | Calabrese |
| 5,632,724 A | 5/1997 | Lerman et al. |
| 5,634,891 A | 6/1997 | Beczak et al. |
| 5,638,588 A | 6/1997 | Jungkind |
| 5,669,116 A | 9/1997 | Jungkind |
| 5,674,187 A | 10/1997 | Zepf |
| 5,681,270 A | 10/1997 | Klearman et al. |
| 5,685,830 A | 11/1997 | Bonutti |
| 5,685,831 A | 11/1997 | Floyd |
| 5,688,137 A | 11/1997 | Bustance |
| 5,690,260 A | 11/1997 | Aikins et al. |
| 5,690,609 A | 11/1997 | Heinze, III |
| 5,693,006 A * | 12/1997 | Slautterback ............ A61F 5/028 224/675 |
| 5,695,452 A | 12/1997 | Grim et al. |
| 5,695,520 A | 12/1997 | Bruckner et al. |
| 5,704,904 A | 1/1998 | Dunfee |
| 5,704,937 A | 1/1998 | Martin |
| 5,708,977 A | 1/1998 | Morkunas |
| 5,718,670 A | 2/1998 | Bremer |
| 5,722,940 A | 3/1998 | Gaylord et al. |
| 5,724,993 A | 3/1998 | Dunfee |
| 5,725,139 A | 3/1998 | Smith |
| 5,728,054 A | 3/1998 | Martin |
| 5,728,168 A | 3/1998 | Laghi et al. |
| 5,732,483 A | 3/1998 | Cagliari |
| 5,735,807 A | 4/1998 | Cropper |
| 5,737,854 A | 4/1998 | Sussmann |
| 5,746,218 A | 5/1998 | Edge |
| 5,752,640 A | 5/1998 | Proulx |
| 5,778,565 A | 7/1998 | Holt et al. |
| 5,782,782 A | 7/1998 | Miller |
| 5,795,316 A | 8/1998 | Gaylord |
| RE35,940 E | 10/1998 | Heinz et al. |
| 5,816,251 A | 10/1998 | Glisan |
| 5,819,378 A | 10/1998 | Doyle |
| 5,823,981 A | 10/1998 | Grim et al. |
| 5,826,766 A | 10/1998 | Aftanas |
| 5,827,211 A | 10/1998 | Sellinger |
| 5,830,167 A | 11/1998 | Jung |
| 5,836,493 A | 11/1998 | Grunsted et al. |
| 5,840,050 A | 11/1998 | Lerman |
| 5,840,051 A | 11/1998 | Towsley |
| 5,848,979 A | 12/1998 | Bonutti et al. |
| 5,853,378 A | 12/1998 | Modglin |
| 5,853,379 A | 12/1998 | Ostojic |
| 5,857,988 A | 1/1999 | Shirley |
| 5,868,292 A | 2/1999 | Stephens et al. |
| 5,890,640 A | 4/1999 | Thompson |
| 5,891,061 A | 4/1999 | Kaiser |
| 5,893,871 A | 4/1999 | Tanaka |
| 5,911,697 A | 6/1999 | Biedermann et al. |
| 5,916,070 A | 6/1999 | Donohue |

(56) References Cited

U.S. PATENT DOCUMENTS

| | | |
|---|---|---|
| 5,938,629 A | 8/1999 | Bloedau |
| 5,950,628 A | 9/1999 | Dunfee |
| 5,954,250 A | 9/1999 | Hall et al. |
| 5,954,253 A | 9/1999 | Swetish |
| 5,967,998 A | 10/1999 | Modglin |
| 5,968,002 A | 10/1999 | Morrisseau |
| 5,993,403 A | 11/1999 | Martin |
| 6,007,503 A | 12/1999 | Berger et al. |
| 6,010,472 A | 1/2000 | Schiller |
| 6,027,466 A | 2/2000 | Diefenbacher et al. |
| 6,029,273 A | 2/2000 | McCrane |
| 6,036,664 A | 3/2000 | Martin et al. |
| 6,039,707 A | 3/2000 | Crawford et al. |
| 6,063,047 A | 5/2000 | Minne |
| 6,066,108 A | 5/2000 | Lundberg |
| 6,070,776 A | 6/2000 | Furnary et al. |
| 6,090,057 A | 7/2000 | Collins et al. |
| 6,099,490 A | 8/2000 | Turtzo |
| 6,110,138 A | 8/2000 | Shirley |
| 6,117,096 A | 9/2000 | Hassard |
| RE36,905 E | 10/2000 | Noble et al. |
| 6,125,792 A | 10/2000 | Gee |
| 6,129,638 A | 10/2000 | Davis |
| 6,129,691 A | 10/2000 | Ruppert |
| 6,156,001 A | 12/2000 | Frangi et al. |
| 6,159,248 A | 12/2000 | Gramnas |
| 6,182,288 B1 | 2/2001 | Kibbee |
| 6,189,538 B1 | 2/2001 | Thorpe |
| 6,190,343 B1 | 2/2001 | Heinz et al. |
| D438,624 S | 3/2001 | Reina |
| 6,206,932 B1 | 3/2001 | Johnson |
| 6,213,968 B1 | 4/2001 | Heinz et al. |
| 6,227,937 B1 | 5/2001 | Principe |
| 6,245,033 B1 | 6/2001 | Martin |
| 6,254,561 B1 | 7/2001 | Borden |
| 6,256,798 B1 | 7/2001 | Egolf et al. |
| 6,267,390 B1 | 7/2001 | Maravetz et al. |
| 6,282,729 B1 | 9/2001 | Oikawa et al. |
| 6,289,558 B1 | 9/2001 | Hammerslag |
| 6,315,746 B1 | 11/2001 | Garth et al. |
| 6,322,529 B1 | 11/2001 | Chung |
| 6,325,023 B1 | 12/2001 | Elnatan |
| 6,338,723 B1 | 1/2002 | Carpenter et al. |
| 6,375,632 B1 | 4/2002 | Albrecht et al. |
| 6,401,786 B1 | 6/2002 | Tedeschi et al. |
| 6,413,232 B1 | 7/2002 | Townsend et al. |
| 6,416,074 B1 | 7/2002 | Maravetz et al. |
| 6,419,652 B1 | 7/2002 | Slautterback |
| 6,425,876 B1 | 7/2002 | Frangi et al. |
| 6,428,493 B1 | 8/2002 | Pior et al. |
| 6,432,073 B2 | 8/2002 | Pior et al. |
| 6,471,665 B1 | 10/2002 | Milbourn et al. |
| 6,478,759 B1 | 11/2002 | Modglin et al. |
| 6,494,853 B1 | 12/2002 | Rossi et al. |
| 6,502,577 B1 | 1/2003 | Bonutti |
| 6,503,213 B2 | 1/2003 | Bonutti |
| 6,508,776 B2 | 1/2003 | Chiang et al. |
| 6,517,502 B2 | 2/2003 | Heyman et al. |
| 6,540,703 B1 | 4/2003 | Lerman |
| 6,589,195 B1 | 7/2003 | Schwenn et al. |
| 6,602,214 B2 | 8/2003 | Heinz et al. |
| 6,605,052 B1 | 8/2003 | Cool et al. |
| 6,609,642 B2 | 8/2003 | Heinz et al. |
| 6,623,419 B1 | 9/2003 | Smith et al. |
| 6,652,596 B2 | 11/2003 | Smith et al. |
| 6,656,144 B1 | 12/2003 | Coligado |
| 6,676,617 B1 | 1/2004 | Miller |
| 6,676,620 B2 | 1/2004 | Schwenn et al. |
| 6,688,943 B2 | 2/2004 | Nagaoka |
| 6,689,080 B2 | 2/2004 | Castillo |
| 6,702,770 B2 | 3/2004 | Bremer et al. |
| 6,711,750 B1 | 3/2004 | Yoo |
| 6,711,787 B2 | 3/2004 | Jungkind et al. |
| 6,726,641 B2 | 4/2004 | Chiang et al. |
| 6,726,643 B1 | 4/2004 | Martin |
| 6,769,155 B2 | 8/2004 | Hess et al. |
| 6,770,047 B2 | 8/2004 | Bonutti |
| 6,773,411 B1 | 8/2004 | Alvarez |
| 6,790,191 B1 | 9/2004 | Hendricks |
| 6,802,442 B1 | 10/2004 | Thompson |
| D499,806 S | 12/2004 | Machin et al. |
| 6,827,653 B2 | 12/2004 | Be |
| D501,078 S | 1/2005 | Cabana |
| 6,893,098 B2 | 5/2005 | Kohani |
| 6,893,411 B1 | 5/2005 | Modglin |
| 6,913,585 B2 | 7/2005 | Salmon et al. |
| 6,921,375 B2 | 7/2005 | Kihara |
| 6,921,377 B2 | 7/2005 | Bonutti |
| 6,923,780 B2 | 8/2005 | Price et al. |
| 6,926,685 B1 | 8/2005 | Modglin |
| 6,936,021 B1 | 8/2005 | Smith |
| 6,942,630 B2 | 9/2005 | Behan |
| 6,951,547 B1 | 10/2005 | Park et al. |
| 6,962,572 B1 | 11/2005 | Zahiri |
| 6,964,644 B1 | 11/2005 | Garth |
| 6,991,611 B2 | 1/2006 | Rhee |
| 7,001,348 B2 | 2/2006 | Garth et al. |
| 7,001,350 B2 | 2/2006 | Grosso |
| 7,025,737 B2 | 4/2006 | Modglin |
| 7,028,873 B1 | 4/2006 | Collier et al. |
| 7,034,251 B1 | 4/2006 | Child et al. |
| 7,048,707 B2 | 5/2006 | Schwenn et al. |
| 7,074,204 B2 | 7/2006 | Fujii et al. |
| 7,083,584 B2 | 8/2006 | Coligado |
| 7,083,585 B2 | 8/2006 | Latham |
| 7,087,032 B1 | 8/2006 | Ikeda |
| 7,101,348 B2 | 9/2006 | Garth et al. |
| 7,118,543 B2 | 10/2006 | Telles et al. |
| 7,128,724 B2 | 10/2006 | Marsh |
| 7,134,224 B2 | 11/2006 | Elkington et al. |
| 7,137,973 B2 | 11/2006 | Plauche et al. |
| 7,140,691 B2 | 11/2006 | Kohani |
| 7,166,083 B2 | 1/2007 | Bledsoe |
| 7,186,229 B2 | 3/2007 | Schwenn et al. |
| 7,198,610 B2 | 4/2007 | Ingimundarson et al. |
| 7,201,727 B2 | 4/2007 | Schwenn et al. |
| 7,235,059 B2 | 6/2007 | Mason et al. |
| 7,281,341 B2 | 10/2007 | Reagan et al. |
| 7,306,571 B2 | 12/2007 | Schwenn et al. |
| 7,306,573 B2 | 12/2007 | Bonutti |
| 7,309,304 B2 | 12/2007 | Stewart et al. |
| 7,316,660 B1 | 1/2008 | Modglin |
| 7,320,670 B1 | 1/2008 | Modglin |
| 7,322,950 B2 | 1/2008 | Modglin |
| 7,329,231 B2 | 2/2008 | Frank |
| 7,331,126 B2 | 2/2008 | Johnson |
| 7,351,368 B2 | 4/2008 | Abrams |
| 7,389,547 B1 | 6/2008 | Wiens |
| 7,402,147 B1 | 7/2008 | Allen |
| 7,404,804 B2 | 7/2008 | Bonutti |
| 7,416,565 B1 | 8/2008 | Al-Turaikl |
| 7,438,698 B2 | 10/2008 | Daiju |
| 7,473,235 B2 | 1/2009 | Schwenn et al. |
| 7,476,185 B2 | 1/2009 | Drennan |
| 7,513,018 B2 | 4/2009 | Koenig et al. |
| 7,549,970 B2 | 6/2009 | Tweardy |
| 7,578,798 B2 | 8/2009 | Rhee |
| 7,591,050 B2 | 9/2009 | Hammerslag |
| 7,597,671 B2 | 10/2009 | Baumgartner et al. |
| 7,597,672 B2 | 10/2009 | Kruijsen et al. |
| 7,600,660 B2 | 10/2009 | Kasper et al. |
| 7,615,021 B2 | 11/2009 | Nordt et al. |
| 7,618,386 B2 | 11/2009 | Nordt et al. |
| 7,618,389 B2 | 11/2009 | Nordt et al. |
| 7,654,972 B2 | 2/2010 | Alleyne |
| 7,662,121 B2 | 2/2010 | Zours |
| 7,670,306 B2 | 3/2010 | Nordt et al. |
| 7,682,219 B2 | 3/2010 | Falla |
| 7,699,797 B2 | 4/2010 | Nordt et al. |
| 7,704,219 B2 | 4/2010 | Nordt et al. |
| 7,727,048 B2 | 6/2010 | Gransberry |
| 7,727,174 B2 | 6/2010 | Chang et al. |
| 7,757,307 B2 | 7/2010 | Wong |
| 7,775,999 B2 | 8/2010 | Brown |

(56) References Cited

U.S. PATENT DOCUMENTS

| | | |
|---|---|---|
| 7,806,842 B2 | 10/2010 | Stevenson et al. |
| 7,815,585 B2 | 10/2010 | Vollbrecht |
| 7,819,831 B2 | 10/2010 | Dellanno |
| 7,833,182 B2 | 11/2010 | Hughes |
| 7,842,000 B2 | 11/2010 | Lai et al. |
| 7,857,776 B2 | 12/2010 | Frisbie |
| 7,862,529 B2 | 1/2011 | Brown |
| 7,862,621 B2 | 1/2011 | Kloos et al. |
| 7,871,388 B2 | 1/2011 | Brown |
| 7,878,998 B2 | 2/2011 | Nordt et al. |
| 7,887,500 B2 | 2/2011 | Nordt et al. |
| 7,914,473 B2 | 3/2011 | Josey |
| D636,494 S | 4/2011 | Garth et al. |
| 7,922,680 B2 | 4/2011 | Nordt et al. |
| 7,950,112 B2 | 5/2011 | Hammerslag et al. |
| 7,954,204 B2 | 6/2011 | Hammerslag et al. |
| 7,959,591 B2 | 6/2011 | Powers et al. |
| 7,993,296 B2 | 8/2011 | Nordt et al. |
| 8,002,724 B2 | 8/2011 | Hu et al. |
| 8,006,877 B2 | 8/2011 | Lowry et al. |
| 8,038,635 B2 | 10/2011 | Dellanno |
| 8,038,637 B2 | 10/2011 | Bonutti |
| 8,047,893 B2 | 11/2011 | Fenske |
| 8,048,014 B2 | 11/2011 | Brown |
| 8,066,161 B2 | 11/2011 | Green et al. |
| 8,066,654 B2 | 11/2011 | Sandifer et al. |
| 8,091,182 B2 | 1/2012 | Hammerslag et al. |
| 8,142,377 B2 | 3/2012 | Garth et al. |
| 8,162,194 B2 | 4/2012 | Gleason |
| 8,162,864 B2 | 4/2012 | Kruijsen et al. |
| 8,172,779 B2 | 5/2012 | Ingimundarson et al. |
| 8,214,926 B2 | 7/2012 | Brown |
| 8,216,167 B2 | 7/2012 | Garth et al. |
| 8,303,528 B2 | 11/2012 | Ingimundarson et al. |
| 8,308,669 B2 | 11/2012 | Nace |
| 8,308,670 B2 | 11/2012 | Sandifer et al. |
| 8,308,869 B2 | 11/2012 | Gardner et al. |
| 8,372,023 B2 | 2/2013 | Garth et al. |
| 8,381,314 B2 | 2/2013 | Takamoto et al. |
| 8,556,840 B2 | 10/2013 | Burke et al. |
| 8,597,222 B2 | 12/2013 | Lucero et al. |
| 8,657,769 B2 | 2/2014 | Ingimundarson et al. |
| 8,728,019 B2 | 5/2014 | Kruijsen et al. |
| 8,795,215 B2 | 8/2014 | Rossi |
| 8,808,213 B2 * | 8/2014 | Hendricks ............... A61F 5/028 602/19 |
| 8,893,312 B2 | 11/2014 | Takamoto et al. |
| 8,956,315 B2 | 2/2015 | Garth et al. |
| 9,370,440 B2 | 6/2016 | Ingimundarson et al. |
| 9,468,554 B2 | 10/2016 | Petursson et al. |
| 9,554,935 B2 | 1/2017 | Ingimundarson et al. |
| 9,572,705 B2 | 2/2017 | Ingimundarson et al. |
| 9,795,500 B2 | 10/2017 | Ingimundarson et al. |
| 2001/0020144 A1 | 9/2001 | Heinz et al. |
| 2001/0031936 A1 | 10/2001 | Pior et al. |
| 2002/0032397 A1 | 3/2002 | Coligado |
| 2002/0068890 A1 | 6/2002 | Schwenn et al. |
| 2002/0148461 A1 | 10/2002 | Heinz et al. |
| 2002/0158097 A1 | 10/2002 | Beale |
| 2002/0165474 A1 | 11/2002 | Chiang et al. |
| 2002/0165475 A1 | 11/2002 | Chiang et al. |
| 2003/0000986 A1 | 1/2003 | Smith |
| 2003/0028952 A1 | 2/2003 | Fujii et al. |
| 2003/0125650 A1 | 7/2003 | Grosso |
| 2003/0125705 A1 | 7/2003 | Ruman et al. |
| 2003/0139698 A1 | 7/2003 | Hyson |
| 2003/0188374 A1 | 10/2003 | Clifton |
| 2003/0220594 A1 | 11/2003 | Halvorson et al. |
| 2003/0229301 A1 | 12/2003 | Coligado |
| 2004/0024340 A1 | 2/2004 | Schwenn et al. |
| 2004/0050391 A1 | 3/2004 | Kiwala et al. |
| 2004/0082895 A1 | 4/2004 | Price et al. |
| 2004/0097857 A1 | 5/2004 | Reinecke et al. |
| 2004/0108350 A1 | 6/2004 | Warren |
| 2004/0116260 A1 | 6/2004 | Drennan |
| 2004/0132380 A1 | 7/2004 | Kihara |
| 2004/0133138 A1 | 7/2004 | Modglin |
| 2004/0143204 A1 | 7/2004 | Salmon et al. |
| 2004/0162582 A1 | 8/2004 | Banziger |
| 2004/0254505 A1 | 12/2004 | Begley et al. |
| 2005/0054960 A1 | 3/2005 | Telles et al. |
| 2005/0059917 A1 | 3/2005 | Garth et al. |
| 2005/0067816 A1 | 3/2005 | Buckman |
| 2005/0081339 A1 | 4/2005 | Sakabayashi |
| 2005/0131323 A1 | 6/2005 | Bledsoe |
| 2005/0137508 A1 | 6/2005 | Miller |
| 2005/0154337 A1 | 7/2005 | Meyer |
| 2005/0160627 A1 | 7/2005 | Dalgaard et al. |
| 2005/0165338 A1 | 7/2005 | Iglesias et al. |
| 2005/0228325 A1 | 10/2005 | Zours et al. |
| 2005/0240134 A1 | 10/2005 | Brown |
| 2005/0251074 A1 | 11/2005 | Latham |
| 2005/0267390 A1 | 12/2005 | Garth et al. |
| 2005/0273025 A1 | 12/2005 | Houser |
| 2006/0011690 A1 | 1/2006 | Bareno |
| 2006/0052733 A1 | 3/2006 | Schwenn et al. |
| 2006/0064048 A1 | 3/2006 | Stano |
| 2006/0074365 A1 | 4/2006 | Brown |
| 2006/0079821 A1 | 4/2006 | Rauch |
| 2006/0129077 A1 | 6/2006 | Parizot |
| 2006/0135900 A1 | 6/2006 | Ingimundarson et al. |
| 2006/0135901 A1 | 6/2006 | Ingimundarson et al. |
| 2006/0135903 A1 | 6/2006 | Ingimundarson et al. |
| 2006/0155229 A1 | 7/2006 | Ceriani et al. |
| 2006/0156517 A1 | 7/2006 | Hammerslag et al. |
| 2006/0206992 A1 * | 9/2006 | Godshaw ............... A61F 5/028 224/904 |
| 2006/0254598 A1 | 11/2006 | Saul |
| 2006/0260620 A1 | 11/2006 | Kazerooni et al. |
| 2007/0152007 A1 | 7/2007 | Kauss et al. |
| 2007/0167895 A1 | 7/2007 | Gramza et al. |
| 2007/0179417 A1 | 8/2007 | Schwenn et al. |
| 2007/0185425 A1 | 8/2007 | Einarsson et al. |
| 2008/0045873 A1 | 2/2008 | Zours |
| 2008/0091132 A1 | 4/2008 | Bonutti |
| 2008/0195010 A1 | 8/2008 | Lai et al. |
| 2008/0208090 A1 | 8/2008 | Vollbrecht |
| 2008/0208091 A1 | 8/2008 | Vollbrecht et al. |
| 2008/0249448 A1 | 10/2008 | Stevenson et al. |
| 2008/0262401 A1 | 10/2008 | Wagner et al. |
| 2008/0302839 A1 | 12/2008 | Murdoch et al. |
| 2008/0319362 A1 | 12/2008 | Joseph |
| 2009/0025115 A1 | 1/2009 | Duffy et al. |
| 2009/0030353 A1 | 1/2009 | Bonutti et al. |
| 2009/0030359 A1 | 1/2009 | Wikenheiser et al. |
| 2009/0062704 A1 | 3/2009 | Brown et al. |
| 2009/0082707 A1 | 3/2009 | Rumsey |
| 2009/0100649 A1 | 4/2009 | Bar et al. |
| 2009/0124948 A1 | 5/2009 | Ingimundarson et al. |
| 2009/0127308 A1 | 5/2009 | Mori et al. |
| 2009/0182253 A1 | 7/2009 | Grim et al. |
| 2009/0192425 A1 | 7/2009 | Garth et al. |
| 2009/0198166 A1 | 8/2009 | Shlomovitz |
| 2009/0275871 A1 | 11/2009 | Liu |
| 2009/0287128 A1 | 11/2009 | Ingimundarson et al. |
| 2010/0010568 A1 | 1/2010 | Brown |
| 2010/0037369 A1 | 2/2010 | Reichert |
| 2010/0100019 A1 * | 4/2010 | Chen ............... A61F 5/03 602/5 |
| 2010/0139057 A1 | 6/2010 | Soderberg et al. |
| 2010/0204630 A1 | 8/2010 | Sandifer et al. |
| 2010/0205713 A1 | 8/2010 | Takamoto et al. |
| 2010/0217167 A1 | 8/2010 | Ingimundarson et al. |
| 2010/0228170 A1 | 9/2010 | Imai |
| 2010/0256717 A1 | 10/2010 | Brown |
| 2010/0268139 A1 | 10/2010 | Garth |
| 2010/0268141 A1 | 10/2010 | Bannister |
| 2010/0274364 A1 | 10/2010 | Pacanowsky et al. |
| 2010/0292622 A1 | 11/2010 | Weissleder et al. |
| 2010/0299959 A1 | 12/2010 | Hammerslag et al. |
| 2010/0318010 A1 | 12/2010 | Sandifer et al. |
| 2011/0000005 A1 | 1/2011 | Brown |
| 2011/0009793 A1 | 1/2011 | Lucero et al. |
| 2011/0046528 A1 | 2/2011 | Stevenson et al. |

(56) References Cited

U.S. PATENT DOCUMENTS

| | | |
|---|---|---|
| 2011/0082402 A1 | 4/2011 | Oddou et al. |
| 2011/0098618 A1 | 4/2011 | Fleming |
| 2011/0105971 A1 | 5/2011 | Ingimundarson et al. |
| 2011/0137221 A1 | 6/2011 | Brown |
| 2011/0144551 A1 | 6/2011 | Johnson |
| 2011/0152737 A1 | 6/2011 | Burke et al. |
| 2011/0178448 A1 | 7/2011 | Einarsson |
| 2011/0184326 A1 | 7/2011 | Ingimundarson et al. |
| 2011/0266384 A1 | 11/2011 | Goodman et al. |
| 2012/0010547 A1 | 1/2012 | Hinds |
| 2012/0022420 A1 | 1/2012 | Sandifer et al. |
| 2012/0029404 A1 | 2/2012 | Weaver et al. |
| 2012/0078151 A1 | 3/2012 | Cropper |
| 2012/0098335 A1 | 4/2012 | Hell et al. |
| 2012/0197167 A1 | 8/2012 | Kruijsen et al. |
| 2012/0204381 A1 | 8/2012 | Ingimundarson et al. |
| 2012/0220910 A1 | 8/2012 | Gaylord et al. |
| 2012/0232450 A1 | 9/2012 | Garth et al. |
| 2012/0245502 A1 | 9/2012 | Garth et al. |
| 2012/0323154 A1 | 12/2012 | Ingimundarson et al. |
| 2013/0006158 A1 | 1/2013 | Ingimundarson et al. |
| 2013/0007946 A1 | 1/2013 | Brown |
| 2013/0012853 A1 | 1/2013 | Brown |
| 2013/0158457 A1 | 6/2013 | Garth et al. |
| 2013/0174326 A1 | 7/2013 | Takamoto et al. |
| 2013/0184628 A1 | 7/2013 | Ingimundarson et al. |
| 2013/0190670 A1 | 7/2013 | Von Zieglauer |
| 2013/0211302 A1 | 8/2013 | Brown |
| 2013/0237891 A1 | 9/2013 | Fryman et al. |
| 2013/0281901 A1 | 10/2013 | Ochoa |
| 2013/0298914 A1 | 11/2013 | Shibaya et al. |
| 2014/0081189 A1 | 3/2014 | Ingimundarson et al. |
| 2014/0116452 A1 | 5/2014 | Ingimundarson et al. |
| 2014/0135672 A1 | 5/2014 | Joseph et al. |
| 2014/0200121 A1 | 7/2014 | Von et al. |
| 2014/0207040 A1 | 7/2014 | Ingimundarson et al. |
| 2014/0207041 A1 | 7/2014 | Ingimundarson et al. |
| 2014/0305982 A1 | 10/2014 | Pelland et al. |
| 2014/0336020 A1 | 11/2014 | Von et al. |
| 2016/0081841 A1 | 3/2016 | Miller et al. |
| 2016/0228279 A1 | 8/2016 | Modglin et al. |
| 2016/0250061 A1 | 9/2016 | Ingimundarson et al. |

FOREIGN PATENT DOCUMENTS

| | | |
|---|---|---|
| CA | 2112789 A1 | 8/1994 |
| CA | 2114387 A1 | 8/1994 |
| CA | 2757353 A1 | 10/2010 |
| CA | 2767353 A1 | 1/2011 |
| CA | 2772296 A1 | 3/2011 |
| CH | 577282 A5 | 7/1976 |
| CH | 612076 A5 | 7/1979 |
| CH | 624001 A5 | 7/1981 |
| CN | 1311648 A | 9/2001 |
| CN | 1383799 A | 12/2002 |
| CN | 1461190 A | 12/2003 |
| CN | 201101603 Y | 8/2008 |
| CN | 101444443 A | 6/2009 |
| CN | 101820783 A | 9/2010 |
| CN | 102470040 A | 5/2012 |
| DE | 1197192 B | 7/1965 |
| DE | 8804683 U1 | 6/1988 |
| DE | 3822113 A1 | 1/1990 |
| DE | 9417221 U1 | 1/1995 |
| DE | 9315776 U1 | 2/1995 |
| DE | 29503552 U1 | 4/1995 |
| DE | 19945045 A1 | 3/2001 |
| DE | 20204747 U1 | 7/2002 |
| DE | 10329454 A1 | 1/2005 |
| DE | 202004015328 U1 | 2/2005 |
| DE | 202005007124 U1 | 6/2005 |
| DE | 102005017587 A1 | 4/2006 |
| DE | 202009004817 U1 | 9/2010 |
| EP | 0393380 B1 | 9/1992 |
| EP | 0589233 A1 | 3/1994 |
| EP | 0614624 A1 | 9/1994 |
| EP | 0614625 A1 | 9/1994 |
| EP | 0657149 A1 | 6/1995 |
| EP | 0589232 B1 | 11/1995 |
| EP | 0693260 B1 | 9/1998 |
| EP | 0651954 B1 | 2/1999 |
| EP | 1016351 A1 | 7/2000 |
| EP | 1159940 A2 | 12/2001 |
| EP | 1236412 A1 | 9/2002 |
| EP | 1342423 A1 | 9/2003 |
| EP | 1588678 A1 | 10/2005 |
| EP | 1743608 A2 | 1/2007 |
| EP | 1985264 A1 | 10/2008 |
| EP | 2200545 A1 | 6/2010 |
| EP | 2451412 A1 | 5/2012 |
| EP | 2473072 A1 | 7/2012 |
| FR | 1104562 A | 11/1955 |
| FR | 2757073 A1 | 6/1998 |
| FR | 2952807 A1 | 5/2011 |
| GB | 0826041 A | 12/1959 |
| GB | 0909970 | 11/1962 |
| GB | 2133289 A | 7/1984 |
| IN | 101219079 A | 7/2008 |
| JP | 07-246212 A | 9/1995 |
| JP | 3031760 U | 12/1996 |
| JP | 09-273582 A | 10/1997 |
| JP | 10-237708 A | 9/1998 |
| JP | 2000-290331 A | 10/2000 |
| JP | 2001-204851 A | 7/2001 |
| JP | 3091470 U | 1/2003 |
| JP | 2003-175063 A | 6/2003 |
| JP | 2004-016732 A | 1/2004 |
| JP | 2004-041666 A | 2/2004 |
| JP | 2004-160075 A | 6/2004 |
| JP | 2004-209050 A | 7/2004 |
| JP | 2007-291536 A | 11/2007 |
| JP | 3142546 U | 6/2008 |
| JP | 2008-178618 A | 8/2008 |
| JP | 2009-082697 A | 4/2009 |
| JP | 2012-011550 A | 1/2012 |
| JP | 2013-503268 | 1/2013 |
| JP | 2013-536010 | 9/2013 |
| WO | 94/01496 A1 | 1/1994 |
| WO | 95/03720 A2 | 2/1995 |
| WO | 97/03581 A1 | 2/1997 |
| WO | 00/53045 A1 | 9/2000 |
| WO | 2004/110197 A2 | 12/2004 |
| WO | 2006/121413 A1 | 11/2006 |
| WO | 2007/003148 A1 | 1/2007 |
| WO | 2005/086752 A3 | 4/2007 |
| WO | 2009/017499 A1 | 2/2009 |
| WO | 2009/017949 A1 | 2/2009 |
| WO | 2009/052031 A1 | 4/2009 |
| WO | 2009/068503 A1 | 6/2009 |
| WO | 2010/141958 A1 | 12/2010 |
| WO | 2011/005430 A1 | 1/2011 |
| WO | 2011/025675 A1 | 3/2011 |
| WO | 2011/066323 A1 | 6/2011 |
| WO | 2012/029917 A1 | 3/2012 |
| WO | 2013/016670 A1 | 1/2013 |
| WO | 2016/138215 A1 | 9/2016 |

OTHER PUBLICATIONS

Hsu et al., "Principles and Components of Spinal Orthoses", AAOS Atlas of Orthoses and Assistive Devices, 4th Ed., Chapter 7, 2008, pp. 89-111.

International Search Report from PCT Application No. PCT/US2018/049969, Nov. 16, 2018.

Mehlman, Charles T. et al., "Hyphenated History: Knight-Taylor Spinal Orthosis"; American Journal of Orthopedics; Jun. 2000; pp. 479-483, vol. 29, Issue 6.

Michael Pfiefer, MD et al., "Effects of a New Spinal Orthosis on Posture, Trunk Strength, and Quality of Life in Women with Postmenopausal Osteoporosis—a Randomized Trial", American Journal of Physical Medicine & Rehabilitation, vol. 83, No. 3, Mar. 2004, USA, pp. 177-186.

(56) References Cited

OTHER PUBLICATIONS

Pamphlet—"Bledsoe Phillippon K.A.F. Positioning Kit, Application Instructions (CP020205 Rev B 04/07), New Hip Arthroscopy Padding and Positioning Kit", Council Directive 93/42/EEC of Jun. 14, 1993 concerning Medical Devices, 2 pages.

Pamphlet—"Bledsoe Phillippon K.A.F. Positioning Kit", Bledsoe Brace Systems, Medical Technology Inc., 2004, 2 pages.

Posture Control Brace. Soll Form, Orthopaedic by Design, FLA Orthopedics, Inc., 1 page; 2004. http://www.flaorthopedics.com.

Sato, Ena et al., "Effect of the Wish-type hip brace on functional mobility in patients with osteoarthritis of the hip:evaluation using the timed Up & Go Test", Prosthetics and Orthotics International 2012 36:25 originally published Jnline Nov. 17, 2011, http://poi.sagepub.com/content/36/125 [retrieved from internet on Jan. 22, 2014].

Scoliosis Specialists. About the SpineCor Brace; 2006-2012; http://www.scoliosisspecialists.com/aboutspinecorbrace.html. Retrieved from Internet on Aug. 1, 2013.

Silosheath Brochure, Soft Socket Gel Liner, 4 pages, 1994.

Spinomed Brochure-Spinal Orthosis for Vertebral Extension in Osteoporosis; Stellar Orthotics and Prosthetics Group, 2 pages, retrieved from Internet Sep. 23, 2013. http://www.stellaroandp.com/spotlight.html.

\* cited by examiner

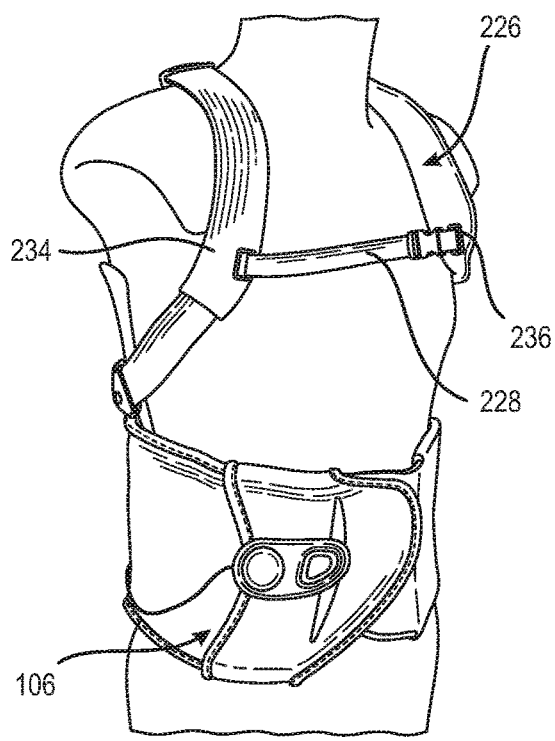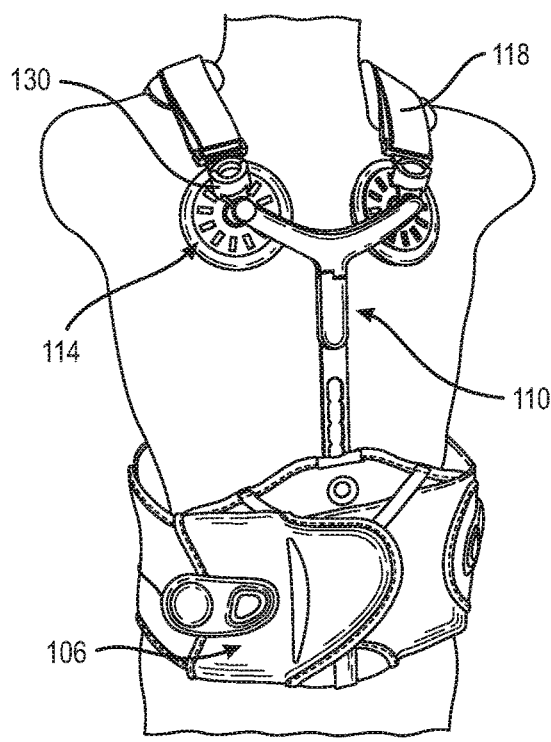
FIG. 10A
FIG. 10B
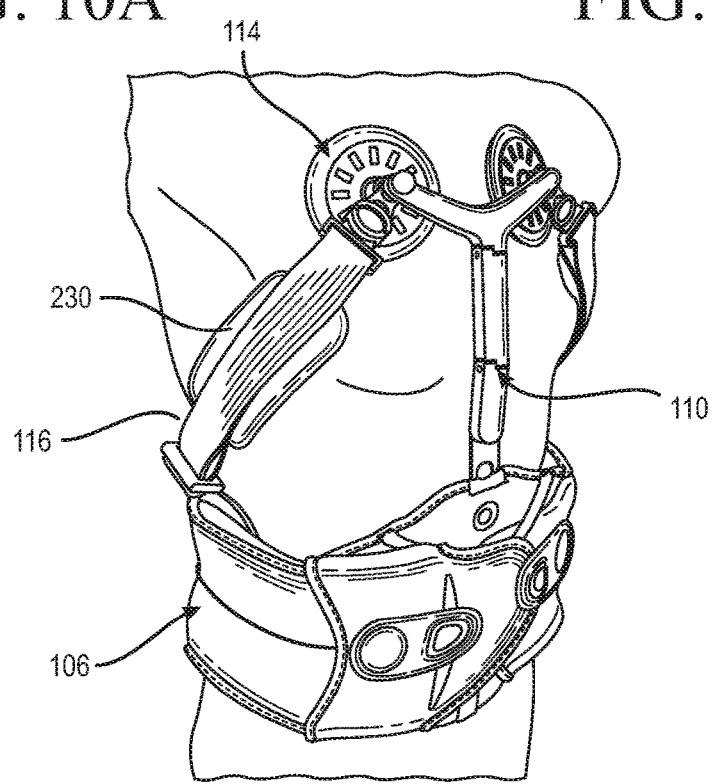
FIG. 10C

THORACIC LUMBAR SACRAL ORTHOSIS ATTACHMENT

CROSS-REFERENCE TO RELATED PATENTS AND APPLICATIONS

This application is a continuation of U.S. application Ser. No. 17/451,927, filed Oct. 22, 2021, which is a continuation of U.S. application Ser. No. 16/124,921, filed Sep. 7, 2018, now U.S. Pat. No. 11,246,734, granted Feb. 15, 2022, which claims priority to U.S. provisional application No. 62/555,482, filed Sep. 7, 2017. This application also incorporates by reference U.S. Pat. No. 8,657,769, granted Feb. 25, 2014, U.S. Pat. No. 8,172,779, granted May 8, 2012, and U.S. patent application publication no. 2016/0250061, published Sep. 1, 2016.

FIELD OF THE DISCLOSURE

The application relates to an orthopedic device, and more particularly to a thoracic lumbar sacral orthosis attachment for a lumbar sacral orthosis, and to a method for configuring the thoracic lumbar sacral orthosis attachment.

BACKGROUND

Spinal orthoses are used to treat many conditions associated with the skeletal structure, including such conditions as osteoporosis, back injuries, chest injuries and spinal deformities, by applying pressure to selected positions along the user's spine, abdomen and torso. There are different spinal orthoses typically categorized by the vertebral level intended for treatment. Spinal orthoses include the sacral orthosis (SO), lumbosacral orthosis (LSO), and the thoracolumbosacral or thoracic lumbar sacral orthosis (TLSO).

The TLSO provides support and immobilization of the thoracic and lumbar regions following various traumatic injuries or surgical procedures. Indications for a TLSO include post-surgical immobilization, herniated disc, spinal stenosis, which occurs when the spinal canal narrows and compresses the spinal cord and nerves, spondylolisthesis which occurs due to anterior displacement of a vertebra or the vertebral column in relation to the vertebrae below, spondylolysis or defects of the vertebra, compression fractures, and degenerative spinal pathologies such as osteoporosis.

Types of TLSO are known in the art. Many TLSOs include flexion control, sagittal control, sagittal-coronal control, and triplanar control such that as a person attempts right or left rotation of the thoracic spine, counterforces from the thoracic band and the subclavicular extension limit motion. There are both commercially available TLSO products, and custom-fabricated TLSO types constructed typically from a rigid thermoplastic to form a body jacket.

While either commercially available or custom orthoses exist, many of these orthoses are uncomfortable to the wearer and difficult to apply. With commercially available TLSO products, some have the tendency to poorly fit the contours of the wearer, including the spine, which results in an ill-fitting TLSO that ineffectively supports the spine. Many TLSO types, particularly custom-fabricated body jackets, are poorly ventilated and lack sufficient padding. They also lack versatility to enable step-up or step-down treatment of the wearer during treatment. Such known TLSO products and custom orthoses are not adaptable to provide different control configurations, and are limited to a single control configuration. Known TLSOs may be configurable to either an over-the-shoulder, or under-the-arm configuration.

Accordingly, there is a need for an improved TLSO with versatile configurations that better fit a user's dynamic needs throughout treatment and without incurring the costs of custom orthoses.

SUMMARY

Under an embodiment of the disclosure, the orthopedic device is configured as a thoracic lumbar sacral orthosis (TLSO) attachment arranged for removably attaching to an orthopedic device, such as a lumbar sacral orthosis (LSO) or torso orthosis, securable about the waist and lumbar region of a user. The TLSO attachment may have an anterior assembly including an anterior panel secured to the LSO, an anterior thoracic extension (ATE) connected to the anterior panel, and a pectoral assembly connected to the ATE. The TLSO attachment may have a posterior assembly connected to the LSO by a posterior panel and includes a posterior thoracic extension (PTE). Either an axillary strap system or a shoulder strap system, or both, may connect to the ATE and the PTE.

The embodiments of the TLSO may be configured to provide gross immobilization of the thoracolumbar spine in all three planes: coronal, sagittal, and transverse. The embodiments offer the ability for a clinician to adapt the TLSO to different strapping configurations including over-the-shoulder or under-the-arm configurations. The embodiments offer improved donning and doffing over known TLSOs, with improved fitting features such as quick-release buckles, slidable straps, and multi-positional attachments.

Because the TLSO attachment connects to an existing LSO or torso orthosis and cervical collar, the attachment can be removed after the wearer no longer has need for a TLSO. This results in a modular system that enables the TLSO attachment to be applied to the LSO when needed, or likewise removed when needed. This results in a step-up and step-down treatment option that better accommodates a user's dynamic needs throughout treatments.

BRIEF DESCRIPTION OF THE DRAWINGS

The orthopedic device is described referring to the accompanying drawings, which show preferred embodiments according to the thoracic lumbar sacral orthosis attachment described herein. The thoracic lumbar sacral orthosis attachment as disclosed in the accompanying drawings is illustrated for example only. The elements and combinations of elements described below and illustrated in the drawings can be arranged and organized differently to result in embodiments still within the spirit and scope of the orthosis described herein.

FIG. 10A is a perspective view of a variation of the TLSO in FIG. 1A having a shoulder strap assembly and without an ATE.

FIG. 10B is a perspective view of the TLSO in FIG. 1A showing only a shoulder strap assembly connected to the ATE.

FIG. 10C is a perspective view of the TLSO in FIG. 1A showing only an axillary strap assembly connected to the ATE.

DETAILED DESCRIPTION OF VARIOUS EMBODIMENTS

The embodiments of the disclosure are particularly adapted for a human body, and may be dimensioned to accommodate different types, shapes and sizes of human body sizes and contours. For explanatory purposes, the orthopedic device embodiments described herein correspond to different sections of a body and are denoted by general anatomical terms for the human body.

The embodiments of the orthopedic device are particularly referred to as corresponding to anterior and posterior body sections by an anterior-posterior plane. The anatomical terms described herein are not intended to detract from the normal understanding of such terms as readily understood by one of ordinary skill in the art of orthopedics.

Embodiments of the orthopedic device described herein may be adapted to the disclosures found in U.S. Pat. No. 8,172,779, and U.S. patent application publication no. 2016/0250061.

Figure 1A:
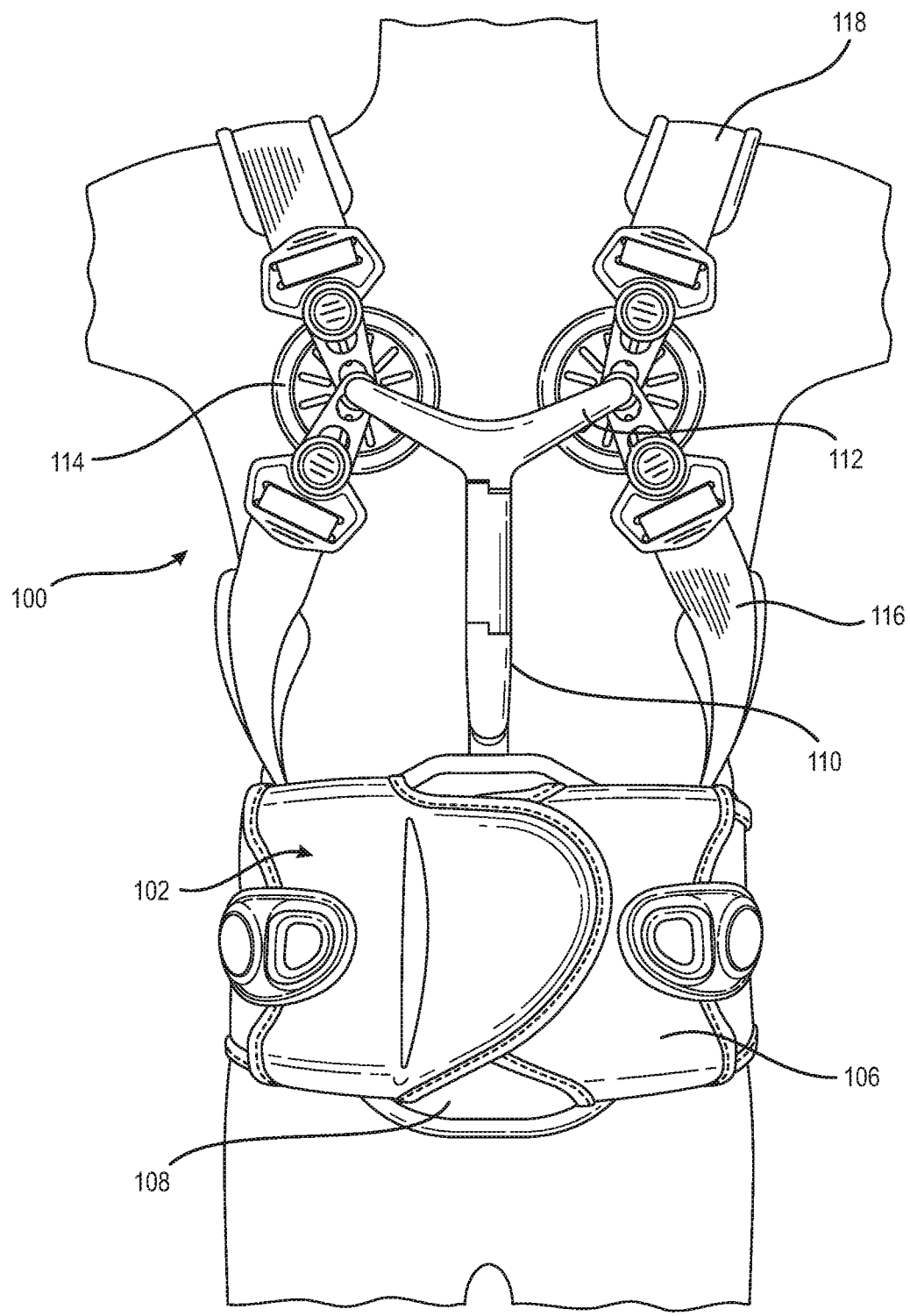
FIG. 1A is a front schematic view of an orthopedic device configured as a thoracic lumbar sacral orthosis (TLSO) with a TLSO attachment connected to a lumbar sacral orthosis (LSO) on a user.

FIG. 1A shows an anterior aspect 102 of an embodiment of an orthopedic device wherein a thoracic lumbar sacral orthosis (TLSO) attachment 100 for configuring a lumbar sacral orthosis (LSO) 106 into a TLSO by connecting the attachment 100 to the lumbar sacral orthosis (LSO) 106. The attachment 100 includes an anterior panel 108 connecting to the LSO 106, an anterior thoracic extension (ATE) 110 secured to the anterior panel 108, a support bar 112 extending from the ATE, at least one pectoral pad 114 secured to the support bar 112, and at least one strap system including an axillary strap system 116 and/or a shoulder strap system 118 connecting to the orthopedic device 106.

The support bar and the at least one pectoral pad, and other features that may become evident from the following disclosure may be adapted from U.S. Pat. No. 8,657,769.

Figure 1B:
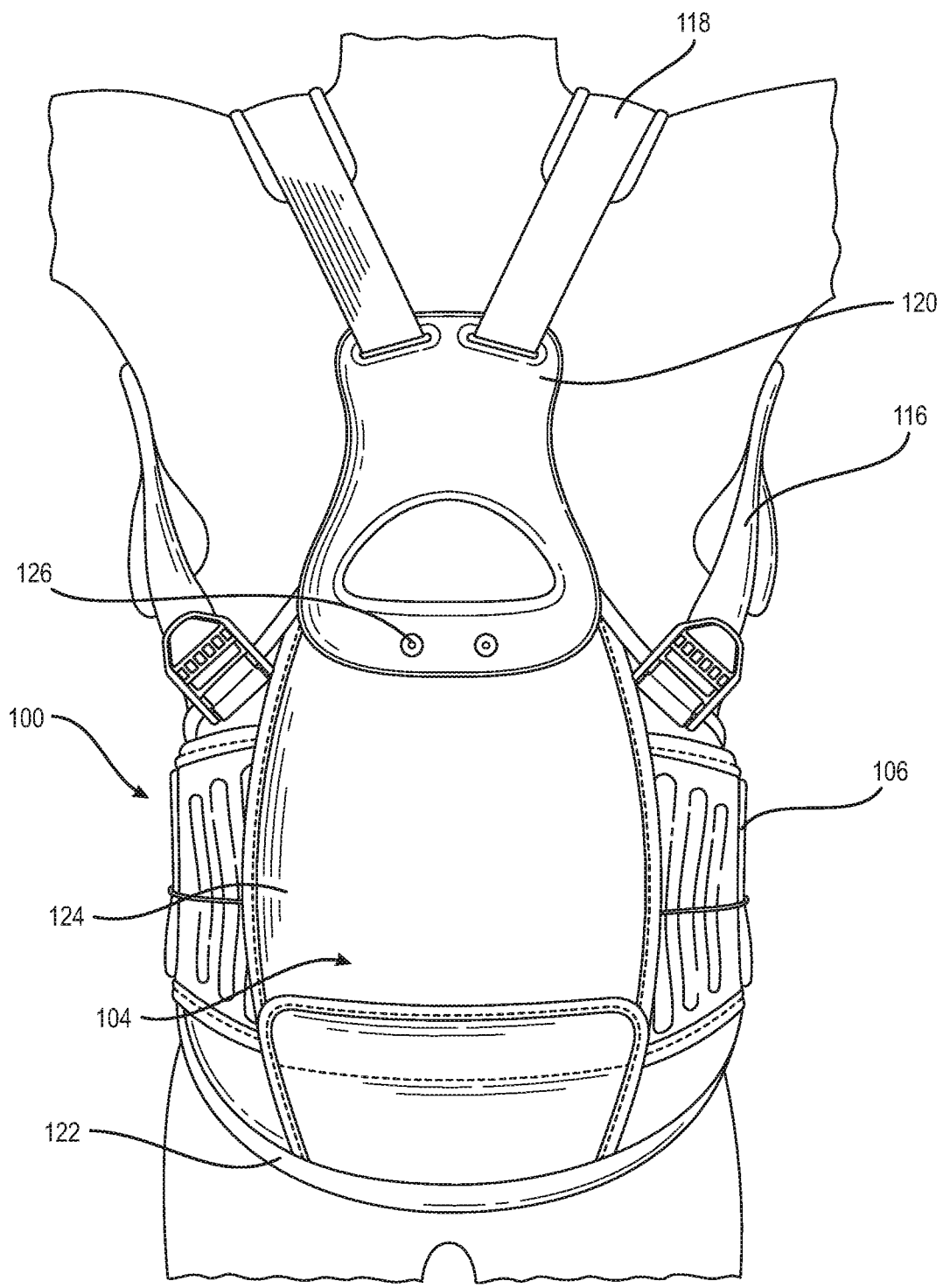
FIG. 1B is a rear schematic view of the TLSO of FIG. 1A on a user.

FIG. 1B shows a posterior aspect 104 of a TLSO attachment 100, and includes a posterior panel 122 having a cover 124 connecting to the LSO/orthopedic device 106, a posterior thoracic extension (PTE) 120 secured to the posterior panel 122, and at least one strap system including an axillary strap system 116 and/or a shoulder strap system 118 connecting to the orthopedic device 106.

Figure 2:
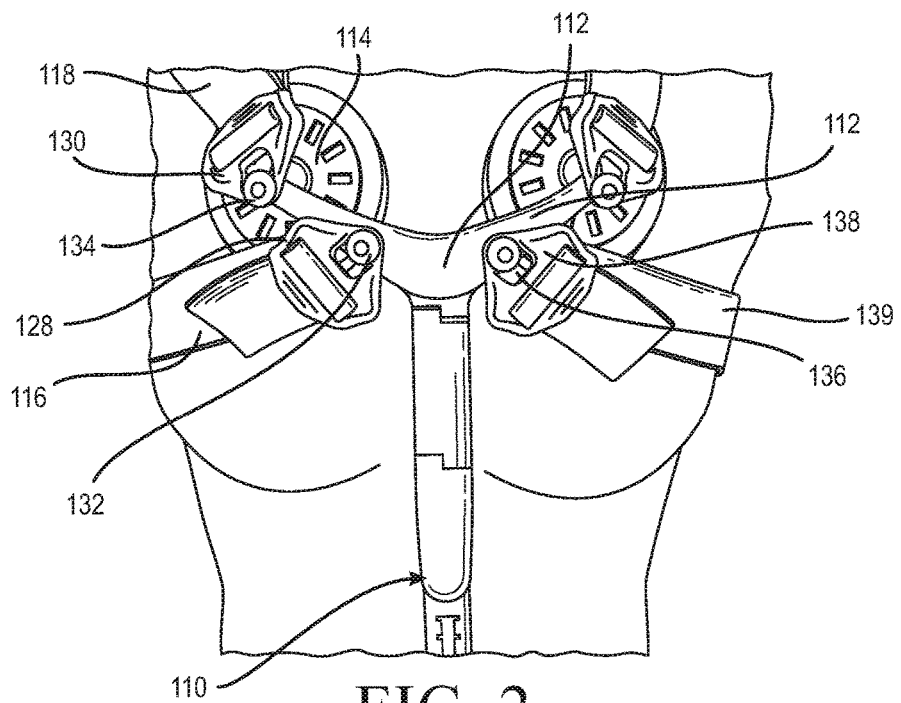
FIG. 2 is a detail view of an embodiment of a pectoral assembly for the TLSO of FIG. 1A.

Referring to FIG. 2, the support bar 112 includes at least one boss 132, 134 protruding from the support bar 112. At least one of the strap systems 116, 118 includes a fastener 128, 130 for removably securing to the at least one boss 132, 134. The at least one boss 132, 134 may include first and second sets of bosses 132, 134, such that the first set of bosses 132 is located closer to the ATE than the second set of bosses 134.

Figure 3A:
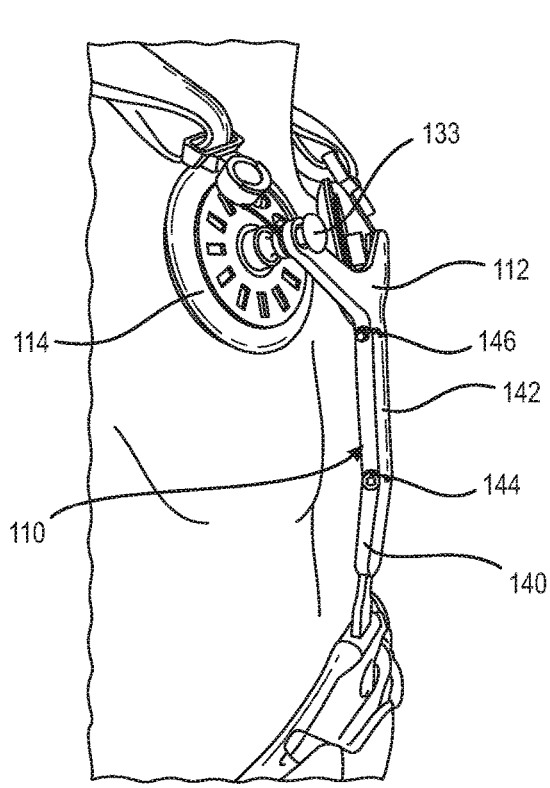
FIG. 3A is a side perspective view of an anterior thoracic extension for the TLSO of FIG. 1A.

At least one boss 133, as shown in FIG. 3A, may be located opposite the pectoral pads, as described in U.S. Pat. No. 8,657,769, to provide alternative relief from a strap system for a user. In any of these variations, there is flexibility on the user for selecting attachment of the strap systems 116, 118 to different locations for comfort and improved immobilization. The axillary strap system 116 may be adapted to secure to the first set of bosses 132 to accommodate a larger arm size.

In the embodiments, fasteners 128, 130 extend from the strap systems 116, 118, and are arranged with an engagement element 138 for receiving a segment 139 of the at least one strap system 116, 118. Each of the fasteners 128, 130 may define a fitting 136, such as a keyhole fitting, arranged for securing about the at least one boss 132, 134 and/or pectoral pads 114.

Figure 3B:
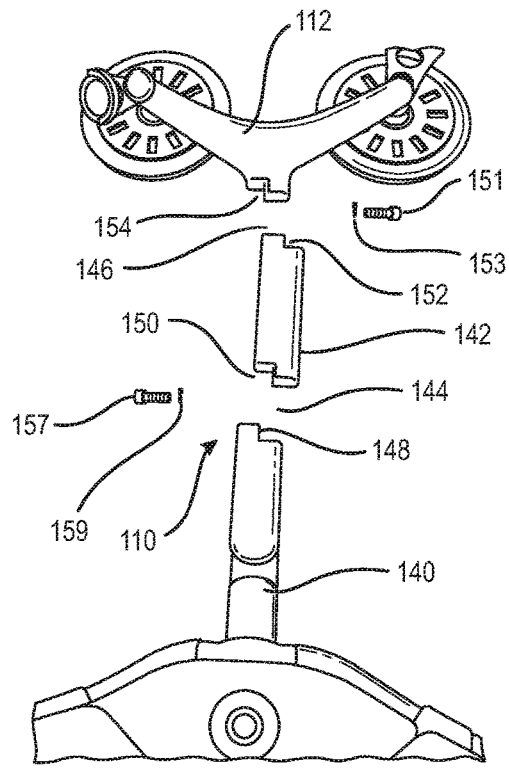
FIG. 3B is an exploded view of the ATE of FIG. 3A.

FIGS. 3A and 3B show how the ATE 110 may comprise first and second parts 140, 142 connected to one another by a first hinge 144, and the second part 142 is hingedly coupled to the support bar 112 at a second hinge 146. The second part 142 is removable so the overall height of the ATE can be shorter based on the dimensions of individual users. A kit may be provided with the second part 142 for added height or additional contourability of the ATE by providing two hinges.

To accommodate the addition or removal of the second part 142, while still offering a hinged ATE 110, the first part 140 preferably has a first interlocking section 148 coupled to a fourth interlocking section 154 extending from the support bar 112 to hingedly connect. The second part 142 has second and third interlocking sections 150, 152 adapted to hingedly couple to the first and fourth interlocking sections 148, 154 of the first part 140 and the support bar 112, respectively.

The hinges 144, 146 may be coupled together by a fastener 151, 157 with a spring bias 153, 159. The hinges 144, 146 or parts thereof, may define a set of teeth engageable with one another, and the coarseness of the teeth may be arranged according to predetermined rotational settings of the hinges 144, 146 of the parts 140, 142, 112 relative to one another.

The first hinge 144 may be formed at a connection between the first part 140 and the second part 142, or at a connection between the first part 140 and the support bar 112. As the second part 142 is removable from the ATE 110 to create a shorter configuration of the ATE110 for shorter users, the first and second hinges 144, 146 are lockable to create custom angles between the first and second parts 140, 142, and the first part 140 or second part 142 between the support bar 112 based on the dimensions of the user.

This arrangement advantageously allows for a user to easily adjust the TLSO attachment to a customized configuration based on the user's dimensions. For example, male and female users, tall and short users, and large and small users easily can adapt the configuration of the hinges 144, 146 and the first and second parts 140, 142 to find the best fit.

Figure 3C:
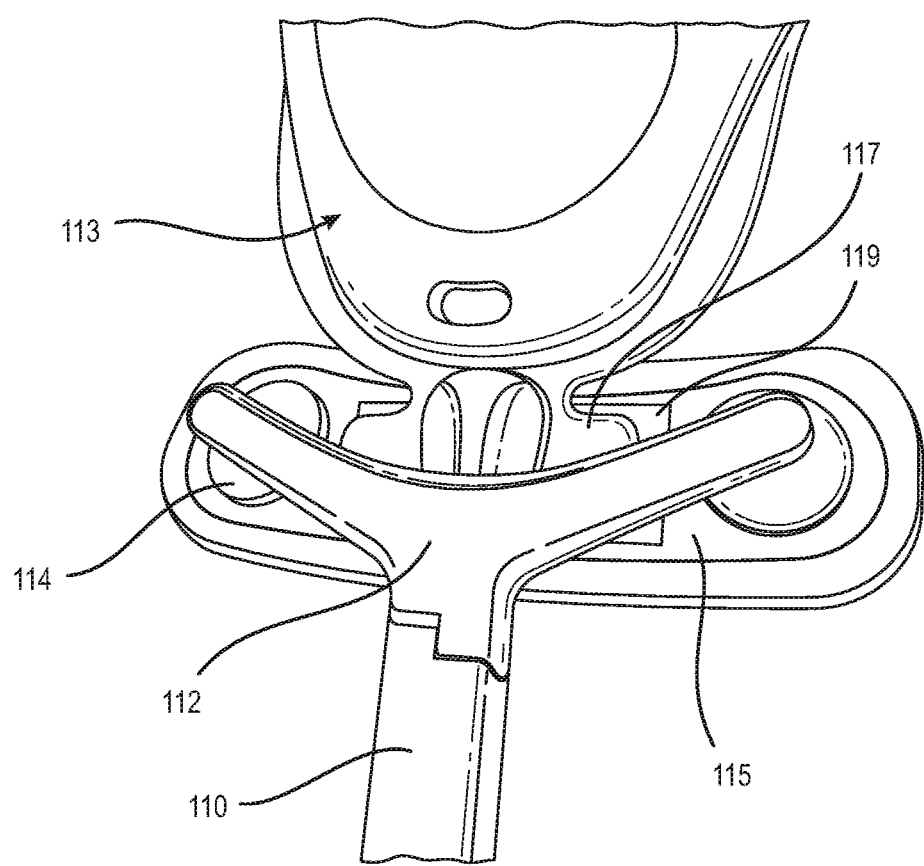
FIG. 3C is a perspective view of an ATE adapted to connect to a cervical collar.

FIG. 3C shows anterior thoracic extension 110 adapted to connect to a cervical collar 113. The support bar 112 connects to a yoke 115 by the pectoral pad 114 by a suitable fastener, such a hook and loop. The cervical collar 113 has a connection 117, such as a thoracic extension, securable to a fastener 119 located on the yoke 115. Fastener 119 may be arranged as a hook island, and a surface of the connection 117 is correspondingly arranged with loop material for removably and conveniently attaching to the hook island, thereby securing the cervical collar 113 to the ATE 110. In this manner, the TLSO can be converted to a cervical-thoracic-lumbar-sacral orthosis that stabilizes the pelvis, back and neck. This arrangement further allows the connection procedure to be simple, intuitive, and repetitive as necessary for individual users.

By providing an attachment as in the embodiment of FIG. 3C that allows for the modular attachment and use of cervical, thoracic, lumbar, and sacral orthopedic devices, individual users are able to dynamically treat a wide variety of pathologies that may change throughout the course of treatment and without the added costs and inconvenience of obtaining custom-fit orthopedic devices.

Figure 3D:
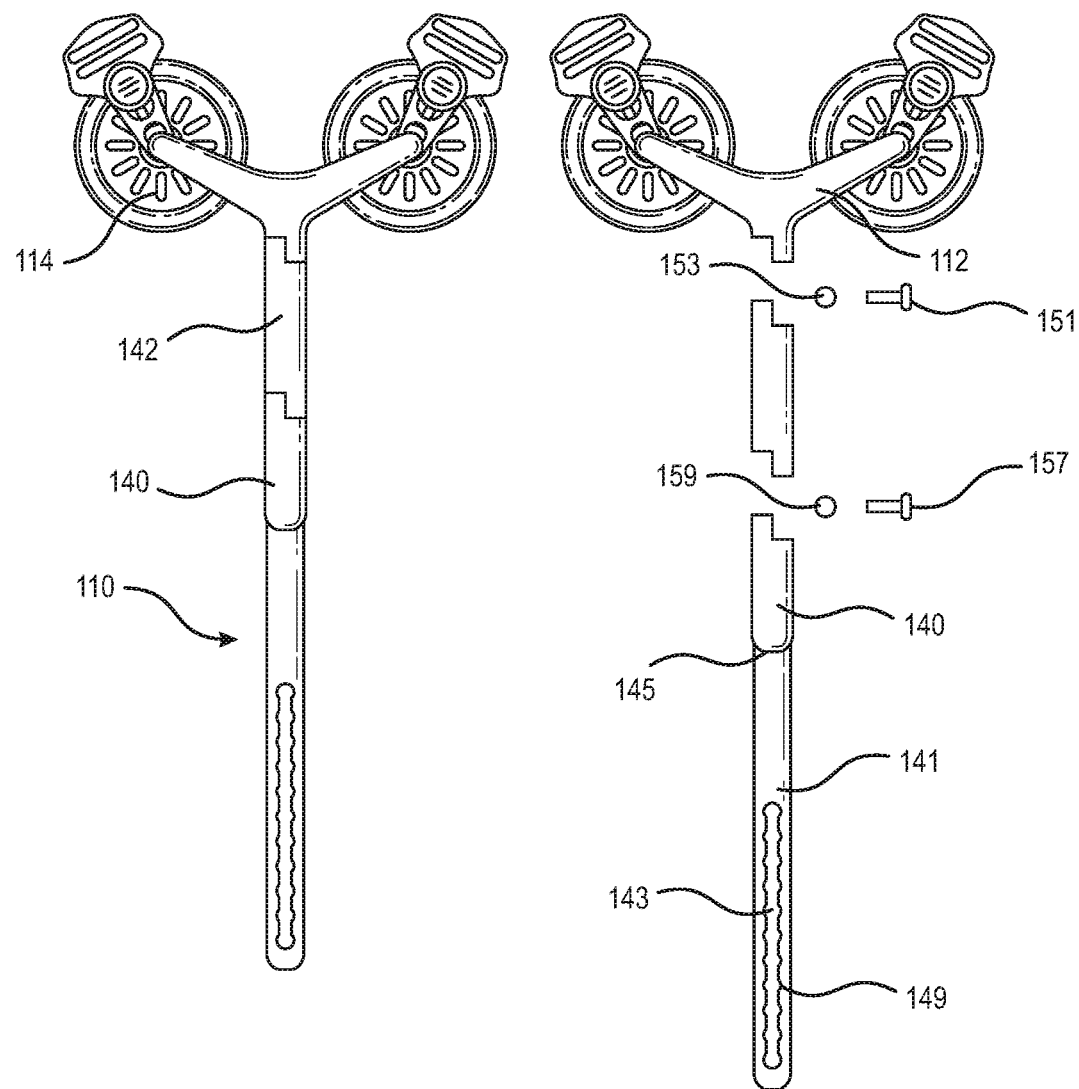
FIG. 3D is a schematic view of an ATE adapted to be adjustable in height by means of an adjustment portion.

FIG. 3D shows an alternative embodiment of anterior thoracic extension 110 configured to be adaptable to a user's height and dimensions by use of an adjustment member 141 extending from the first part 140 at a juncture 145. In the embodiment of FIG. 3D, the juncture 145 is not a hinged attachment, but in other embodiments may be arranged as a hinge like first and second hinges 144, 146 in order to better fit a user's dimensions via a third degree of rotation.

Adjustment member 141 is configured as a strut and contains an adjustment slot 143 which may define discrete settings or heights from which a user may select. The discrete settings may be defined by a toothed surface 149 as seen in FIG. 3D, with individual teeth of the toothed surface 149 corresponding to a desired height. In certain embodiments, indicia may be provided on a surface of the adjustment member 141 for indicating the height setting currently being used. The adjustment slot 143 may be alternatively configured in other manners that achieve the function of allowing for optimal height adjustment of the ATE 110.

The adjustment member 141 may translate up and down through a channel (not shown) defined by a portion of the anterior panel 108 with removable fastening means for securing the ATE 110 at a desired height setting. By providing adjustment member 141, the ATE 110 may be positioned at the optimal location along a user's torso, allowing the user or a clinician assisting the user to finely position one of the hinges 144, 146, the pectoral bar 112, the pectoral pads 114, or the strap systems 116, 118 at the ideal location based on the user's movements and dimensions.

Figure 3E:
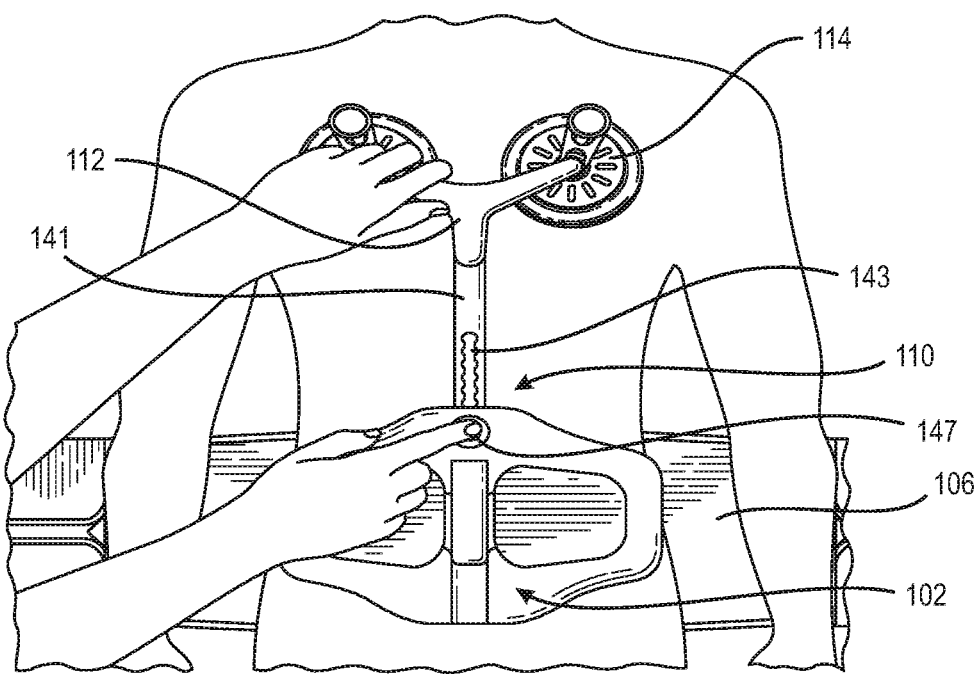
FIG. 3E is a schematic view of the ATE of FIG. 3D arranged with a TLSO attachment.

FIG. 3E shows the ATE 110 of FIG. 3D arranged on a user, with adjustment member 141 and adjustment slot 143 configured to be adjusted through the use of a button 147. In the depicted embodiment, button 147 may be arranged with a removable fastener (not shown) that releases the adjustment member 141 when the button is depressed, allowing a user or a clinician to freely slide the adjustment member 141 up or down as needed to obtain an optimal height of the ATE 110. When the optimal height has been attained, the button 147 may be released, allowing an automatic biasing mechanism to apply the removable fastener to secure the adjustment member 141 at the selected height setting.

The arrangement of the button 147 allows for intuitive adjustment of the height of the ATE 110 that allows for the ATE 110 to be positioned where needed based on the user's dimensions and stage of treatment. The arrangement further allows for the ATE 110 to be assembled simply and modularly with the TLSO attachment and the orthopedic device 106.

Figure 3F:
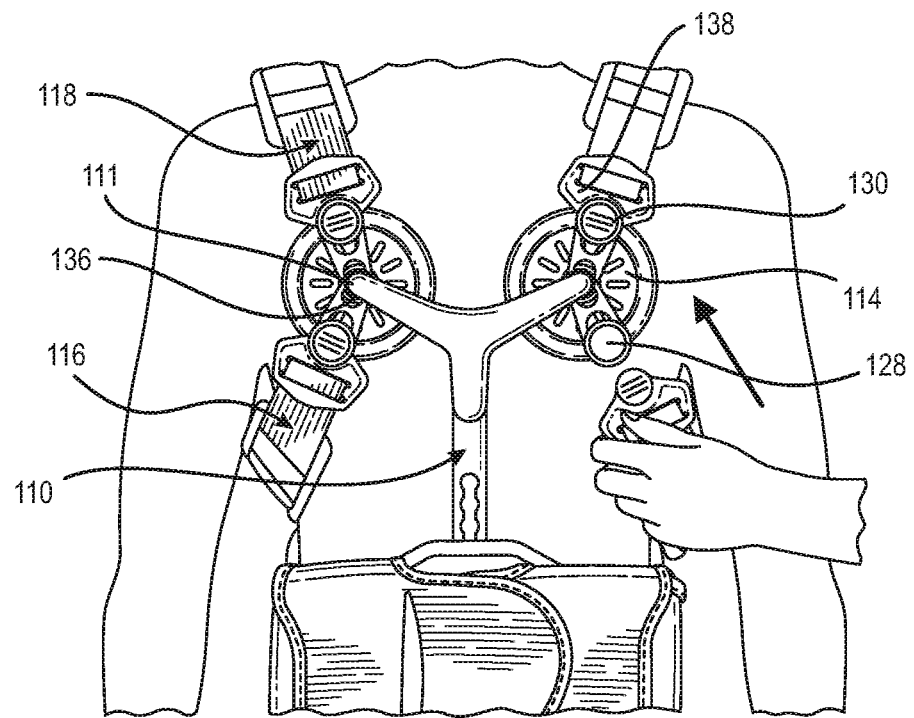
FIG. 3F is a schematic view of the ATE of FIG. 3D connected to strap systems via a single boss.
Figure 3G:
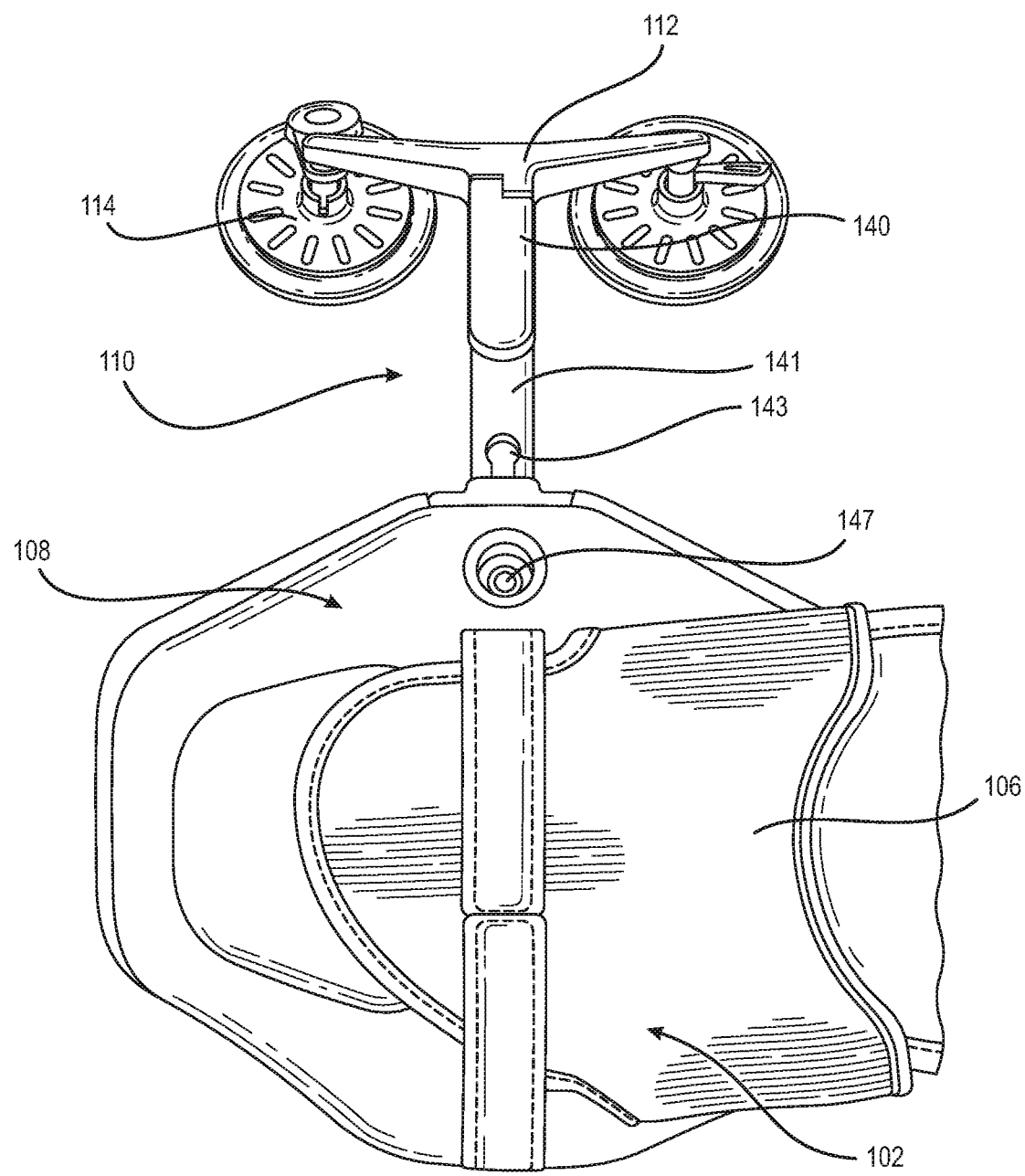
FIG. 3G is a schematic view of the ATE of FIG. 3D arranged with a TLSO attachment and an orthopedic device and configured for a shorter user.

The embodiment of FIG. 3E is shown further in FIG. 3F, which illustrates an arrangement of strap systems 116, 118 about the ATE 110. The strap systems 116, 118 may attach about a same boss 111, at which the pectoral pads 114 may also be attached to the pectoral bar 112, allowing for a simple, robust, and intuitive assembly of the device, especially as the strap systems 116, 118 are engaged over the user's shoulders and under the user's arms.

Figure 4A:
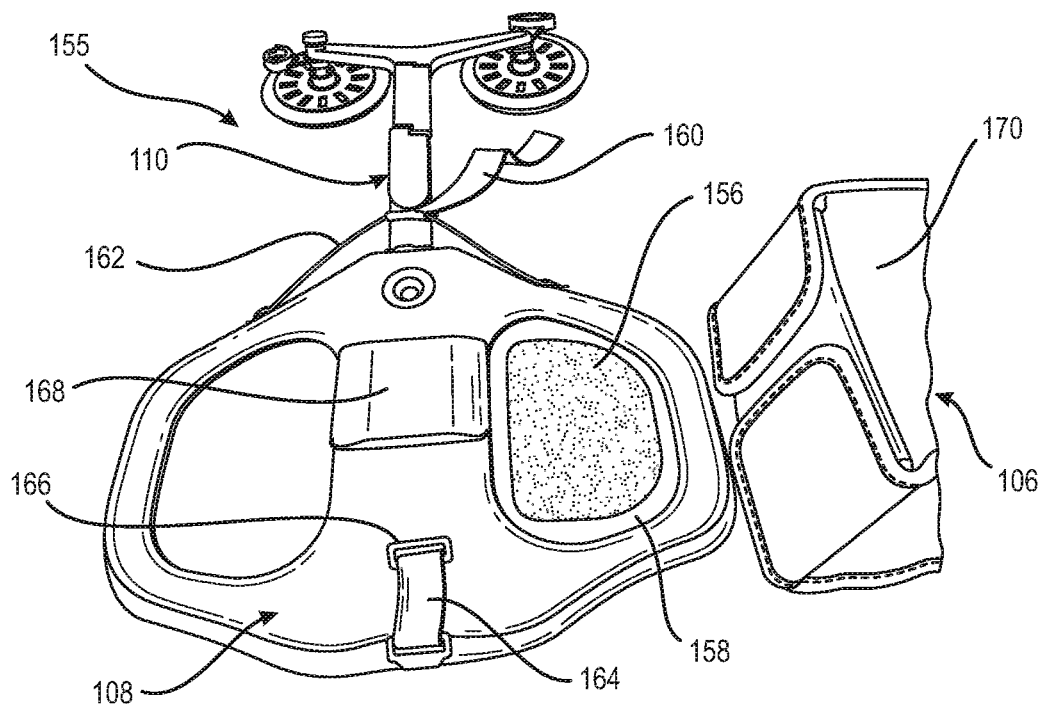
FIG. 4A is a schematic view of a first step of connecting an anterior panel attachment system for connecting an anterior panel to an orthopedic device in the TLSO of FIG. 1A.
Figure 4B:
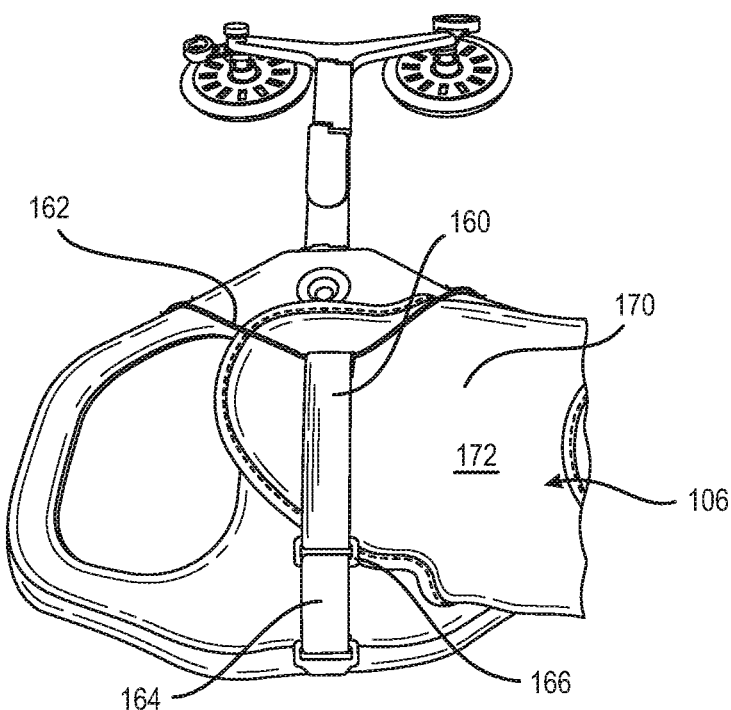
FIG. 4B is a schematic view of a second step of connecting the anterior panel to the orthopedic device in the TLSO of FIG. 4A.

FIGS. 4A and 4B show an embodiment of an anterior attachment system 155 including at least one side fastener 156, such as a patch having hook material that may be in a cut-away 158 of the anterior panel 108, secured to a side of the anterior panel 108, and a central fastener 168 generally centrally secured to the anterior panel 108 for providing lateral attachment to an anterior section of the orthopedic device 106.

The anterior attachment system 155 further comprises a longitudinal attachment to the orthopedic device 106 with a first strap 160 extending from a top portion of the anterior panel 108. The first strap may be tethered by at least one tether 162 extending toward a second strap 164 and coupling therewith with a coupler 166 extending from the second strap 164 to form a loop for securing to an anterior section, such as a belt member 170, of the orthopedic device 106. A surface 172 of the belt arm is preferably engageable with the at least one side fastener 156 and the central fastener 168. In this manner, the TLSO attachment is easily combined with a variety of existing lumbar support orthoses. The side and central fasteners 156, 168 and the longitudinal attachment system are broadly compatible with and adaptable for existing devices and offer a secure attachment system on both inward- and outward-facing surfaces of the lumbar support orthoses without the need for custom configurations.

Figure 4C:
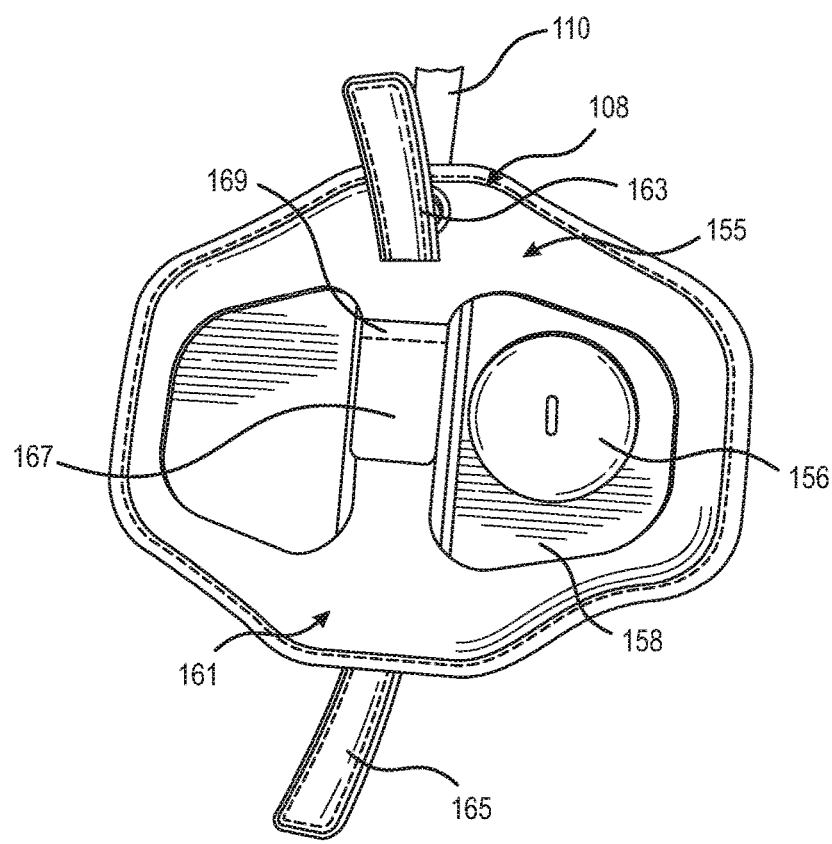
FIG. 4C is a schematic view of an alternative embodiment of an anterior panel attachment system for connecting an anterior panel to an orthopedic device in the TLSO of FIG. 1A.
Figure 4D:
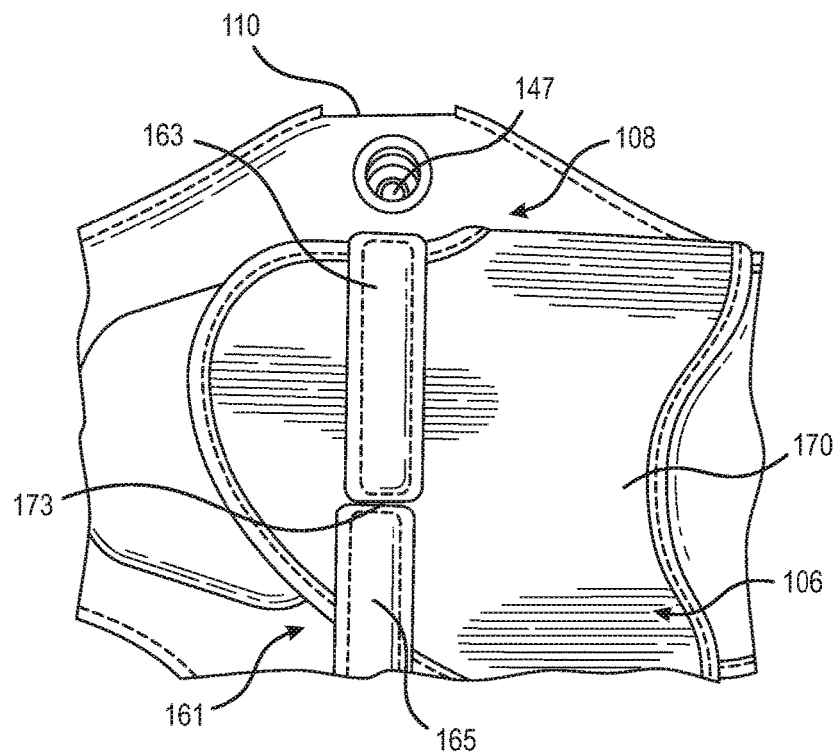
FIG. 4D is a schematic view of the anterior panel attachment system of FIG. 4C.
Figure 5A:
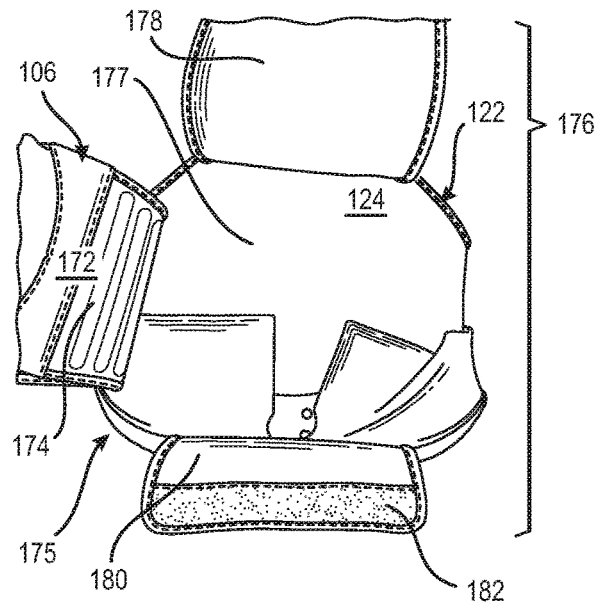
FIG. 5A is a schematic view of a first step of using a posterior panel attachment system for connecting an anterior panel to the orthopedic device in the TLSO of FIG. 1B.
Figure 5B:
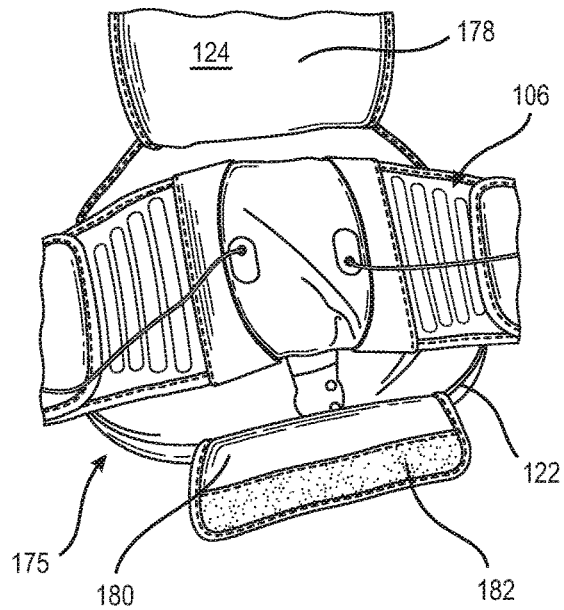
FIG. 5B is a schematic view of a second step of connecting a posterior panel attachment system to the orthopedic device in FIG. 5A.
Figure 5C:
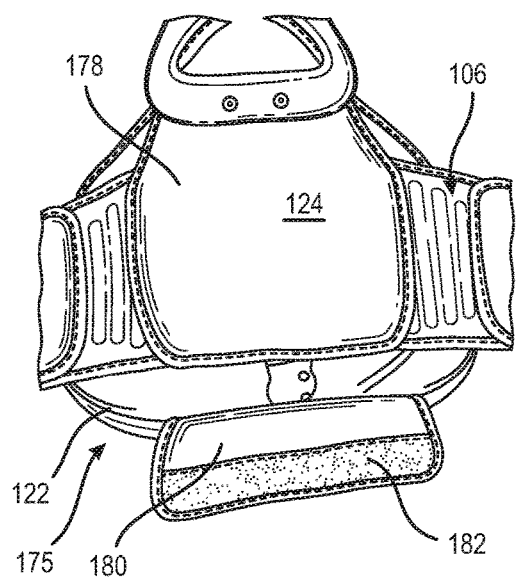
FIG. 5C is a schematic view of a third step of connecting a posterior panel attachment system to the orthopedic device in FIG. 5A.
Figure 5D:
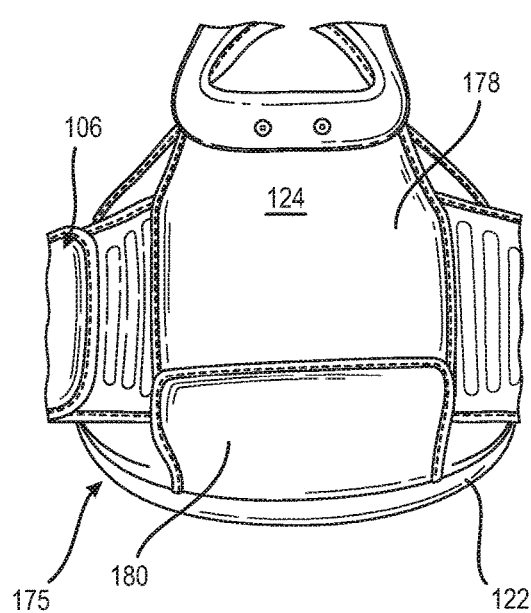
FIG. 5D is a schematic view of a fourth step of connecting a posterior panel attachment system to the orthopedic device in FIG. 5A.

FIGS. 4C-D show an alternative embodiment of the anterior attachment system 155, wherein the anterior panel 108 receives and secures to an orthopedic device via top and bottom fasteners 163, 165 which attach over the orthopedic device 106 (for example a lumbar sacral orthosis belt) and secure at an outer-facing surface thereof via fasteners, which in this embodiment may be hook and loop fasteners. Additionally, a central fastener 167 attaches to an inner-facing surface of the orthopedic device 106, in this embodiment also hook and loop fastener. The top and bottom fasteners 163, 165 attach independently of each other, allowing for flexibility, intuitiveness, and simplicity in how the straps are arranged over the orthopedic device 106. The top and bottom fasteners 163, 165 may be arranged in length to abut one another at a junction or point 173.

This arrangement allows the top and bottom fasteners 163, 165 to effectively provide a complete longitudinal engagement with the orthopedic device 106 without having to physically couple the top and bottom fasteners 163, 165 with each other via another fastening device. As with the embodiment in FIGS. 4A-B, a side fastener 156 may be arranged at a cutout 158 for additional stabilization, especially in the axial direction. Cutout 158 may be arranged with a sufficient size to allow the side fastener 156 or additional side fasteners to be arranged in a variety of configurations deemed advantageous for a particular use.

FIGS. 5A-5D show an embodiment of a posterior attachment system 175 for securing to a posterior section of the orthopedic device 106, and includes a cover 176 extending over the posterior panel 122. The cover 176 has a central fastener 177 for engaging a surface 172 of a posterior section 174 of the orthopedic device 106 to laterally secure the orthopedic device 106 to the posterior panel 122. The cover 176 has a first flap 178 defining a portion of cover 124 extending over the posterior section 174 of the orthopedic device 106, and a second flap 180 having a fastener 182 engaging the first flap 178 to longitudinally secure the orthopedic device 106 to the posterior panel 122.

Like the anterior attachment system 155 depicted in FIGS. 4A and 4B, the posterior attachment system 75 is configured to be broadly compatible with and adaptable to existing lumbar sacral orthoses of different sizes and configurations. The central fastener 177 and the first and second flaps 178, 180 serve to effectively secure the TLSO attachment to the existing lumbar sacral orthosis on both inward- and outward-facing surfaces thereof.

Figure 6A:
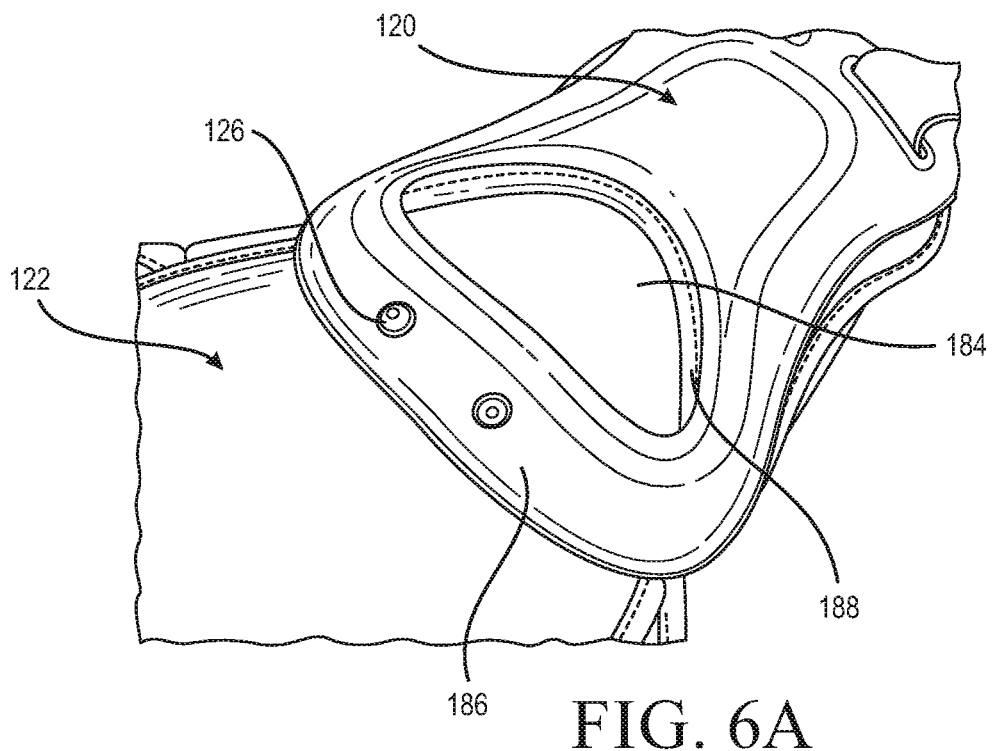
FIG. 6A is a schematic view of a posterior thoracic extension (PTE) connected to a posterior panel.
Figure 6B:
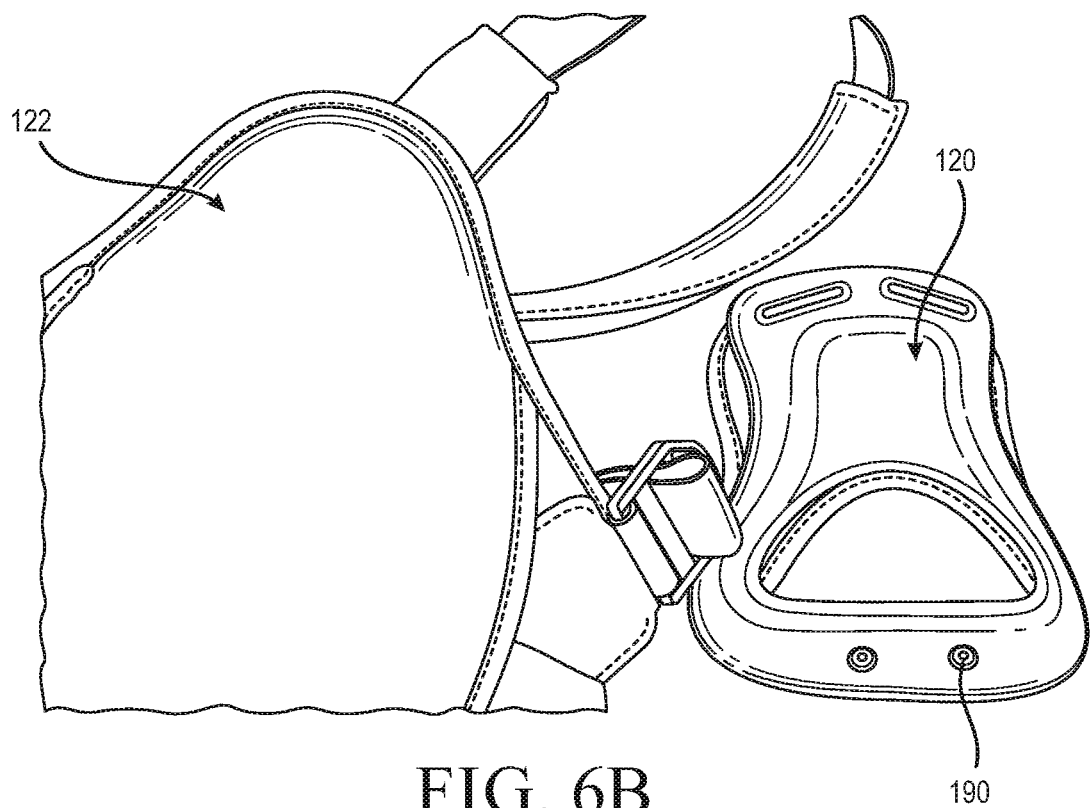
FIG. 6B is a schematic view of the PTE removed from the posterior panel.

FIGS. 6A and 6B depict an embodiment of a PTE, wherein the PTE 120 secures to a crest 184 of the posterior panel 122. The PTE 120 defines a shell having an opening 188 generally extending about a portion of the crest 184 and a bar 186 adapted for receiving fasteners 126 engageable with the posterior panel 122. Bar 186 defines at least one aperture 190 for receiving fasteners 126. If extra height of the PTE is desired relative to the posterior panel 122, the PTE 120 may be inserted over the crest 184 of the posterior panel 122 via the opening 188 such that the bar 186 will reside at a higher location relative to the crest 184 than the fasteners 126 with the PTE 120 being wedged onto the crest 184 of the posterior panel 122. This arrangement of the PTE 120 allows for a user-specific adjustment of the height of the PTE relative to the user and the posterior panel 122 with a simplified procedure for securing the device together, as the fasteners 126 are easily adaptable to secure through the posterior panel 122 at any convenient location to engage the at least one aperture 190.

Figure 7A:
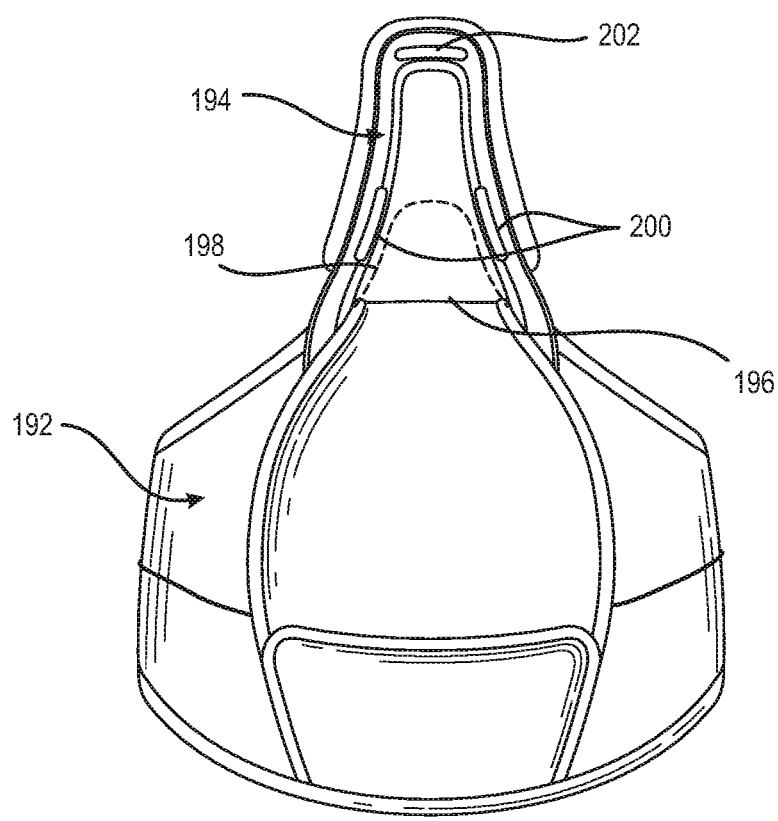
FIG. 7A is an elevational view showing another embodiment of a PTE connected to a posterior panel.

FIG. 7A exemplifies how the PTE 194 secures to a crest 198 of a posterior panel 192 by a slot 196 formed by the PTE 194. The PTE 194 overlaps with the crest 198, and the PTE 194 may be secured to the posterior panel 192 by fasteners or by being wedged. In this embodiment, the PTE 194 defines at least one side slot 200 and at least one end slot 202 for receiving strap segments. Returning to FIG. 1B, the axillary strap system 116 may secure to the PTE 194 by the at least one side slot 200, and the shoulder strap system 118 may secure to the at least one end slot 202.

Figure 7B:
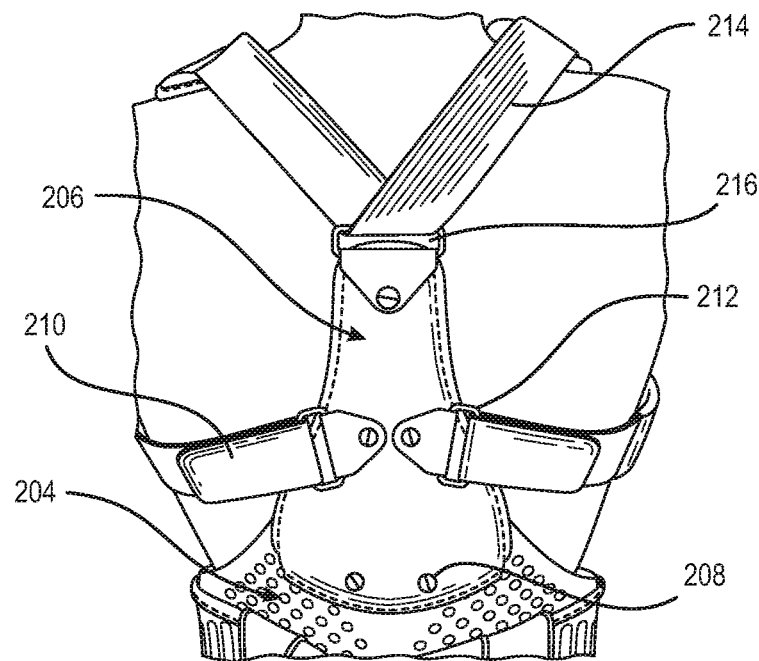
FIG. 7B is a schematic view showing yet another embodiment of a PTE connected to a posterior panel.

FIG. 7B shows how the PTE 206 may overlap a posterior panel 204, and is secured thereto by fasteners 208. At least one side ring, bracket or buckle 212 may be pivotally secured to the PTE 206 for receiving a strap segment 210, and at least one end ring, bracket or buckle 216 may be pivotally secured to the PTE 206 for receiving a strap segment 214. For example, returning to the embodiment of FIG. 1B, bracket 212 may receive axillary strap system 116 at the at least one side ring, bracket or buckle 212. Shoulder strap system may be received at the at least one side ring, bracket or buckle 216. Alternatively, PTE 206 may be arranged in a system without an ATE, wherein strap segments 210 and 214 connected by wrapping around the user's shoulders.

PTE 206 may adapt to a user's movements and specific dimensions by providing that the at least one side ring, bracket, or buckle 212, 216 are pivotally attached to the PTE 206. As a user moves, the strap attachments may accordingly pivot to a desired degree on the PTE 206 in order to accommodate the motion and the user's dimensions.

Figure 8A:
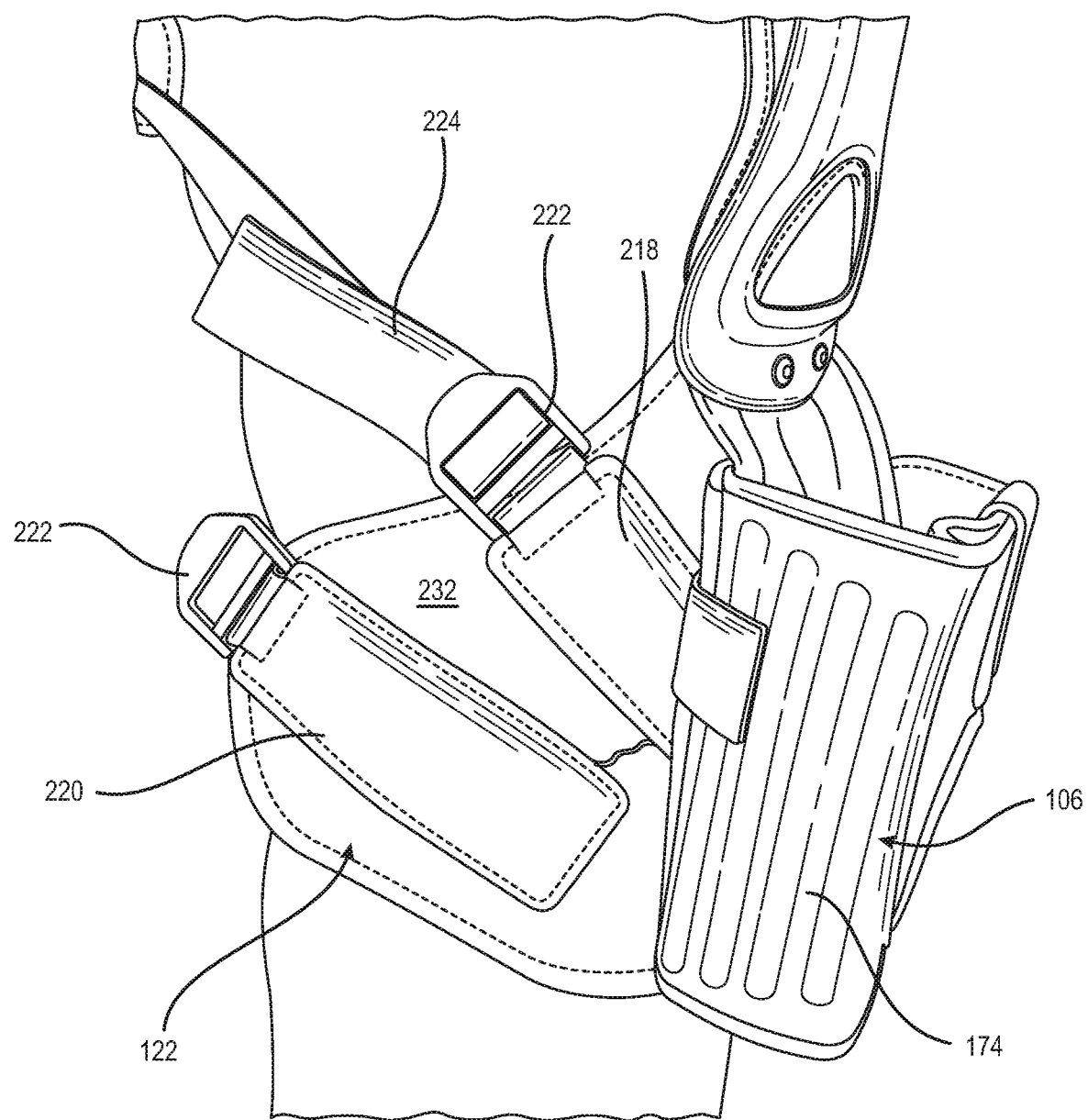
FIG. 8A is a schematic view showing a versatile strap mount system for connecting an axillary strap system to a posterior panel.

Referring to FIG. 8A, at least one strap mount 218, 220 may be removably attachable to a surface 232 of the posterior panel 122, such that a posterior section 174 of the orthopedic device 106 overlaps the at least one strap mount 218, 220. The at least one strap mount 218, 220 may be removably attachable over the entire surface 232. For example, the at least one strap mount 218, 220 may include a hook material engageable with a loop material extending from the surface 232. The at least one strap mount 218, 220 may define a strap attachment 222 extending from the at least one strap mount 218, 220 for receiving a strap segment 224 to a strap system.

The at least one strap mount is provided to attach a strap to the PTE according to the anatomy of the user, since the strap, particularly an axillary strap system, may be uncomfortable to some users under the armpit, such that the axillary strap system is arranged to be more comfortable to the user while still possessing the function of immobilization and accommodating a user's morphology.

Figure 8B:
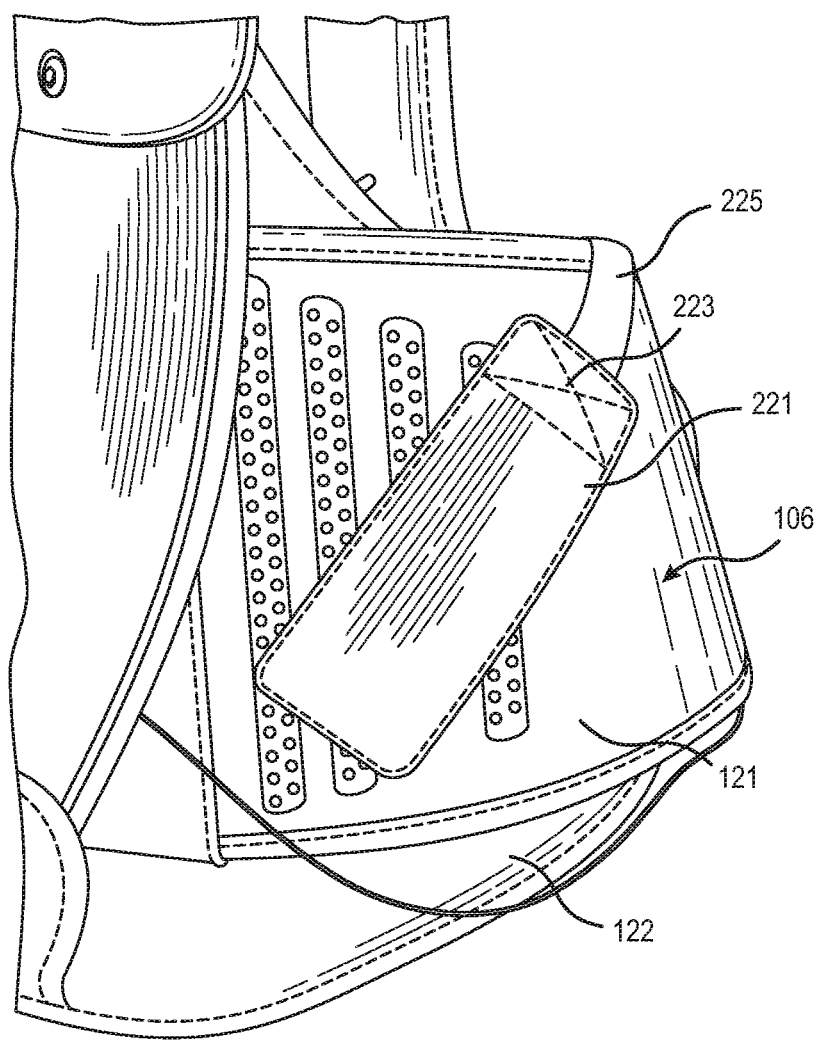
FIG. 8B is a schematic view showing an alternative embodiment of a versatile strap mount for connecting an axillary strap system to a posterior panel.

FIG. 8B depicts an alternative embodiment of a strap mount 221 arranged to be removably attached to an exterior surface material 121 of the orthopedic device 106 as opposed to the posterior panel 122. This arrangement allows for added convenience as a user is able to easily adjust the position of the strap mount for optimal comfort and fit without having to remove or decouple the posterior attachment system 175 from the orthopedic device 106.

Strap mount 221 is coupled to a strap segment 225 by a reinforcement portion 223, wherein additional stitching and strong stitching patterns enable a more robust connection between the material of the strap mount 221 and the strap segment 225. Strap mount 221 is arranged with a fastener such as a hook and loop fastener allowing for attachment of the strap mount 221 to an outer surface material 121 of the orthopedic device 106.

Figure 9A:
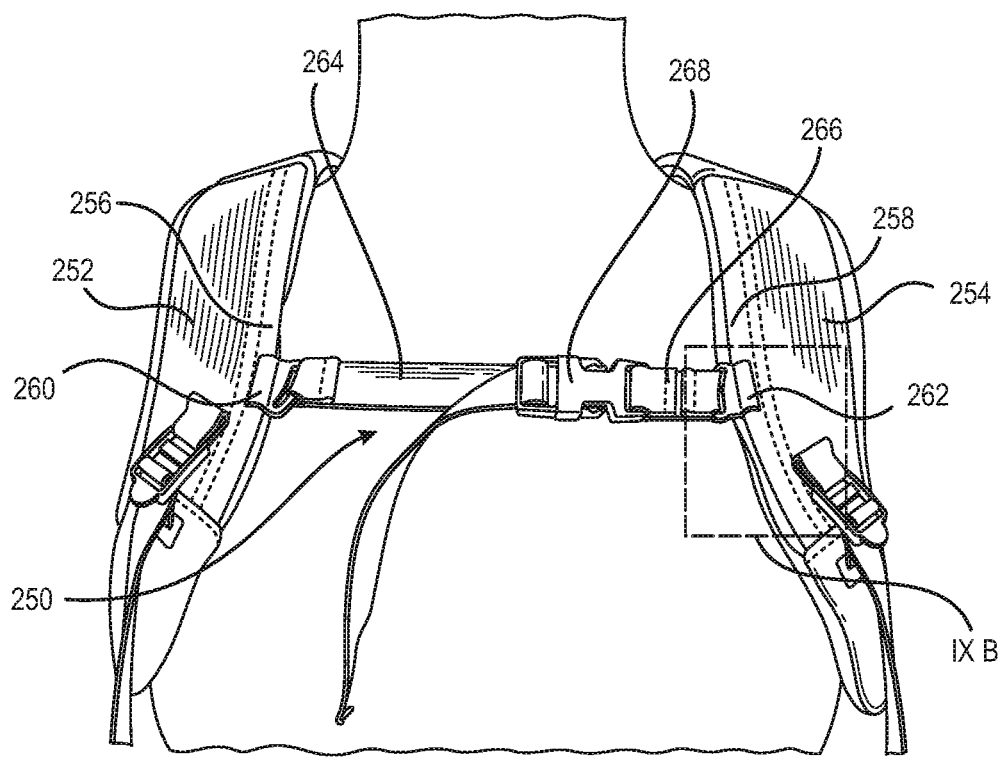
FIG. 9A is a schematic view showing a variably positioned sternum strap.

FIG. 9A depicts a chest strap 250 adjustable along a user's chest and relative to first and second straps 252, 254. The anterior side of the first and second straps 252, 254 includes reinforced edges 256, 258, respectively, upon which the first and second sliders 260, 262 slide along, respectively. First and second strap segments 264, 266 are coupled by a buckle 268, and each of the first and second strap segments 264, 266 are tethered to the first and second sliders 260, 262. The arrangement of the embodiment in FIG. 9A allows the chest strap 250 to not only assure that the shoulder straps 252, 254 are retained in proper position over the user's shoulders but also the device to adjust for ideal comfort based on the user's characteristics, e.g. between male and female users.

Figure 9B:
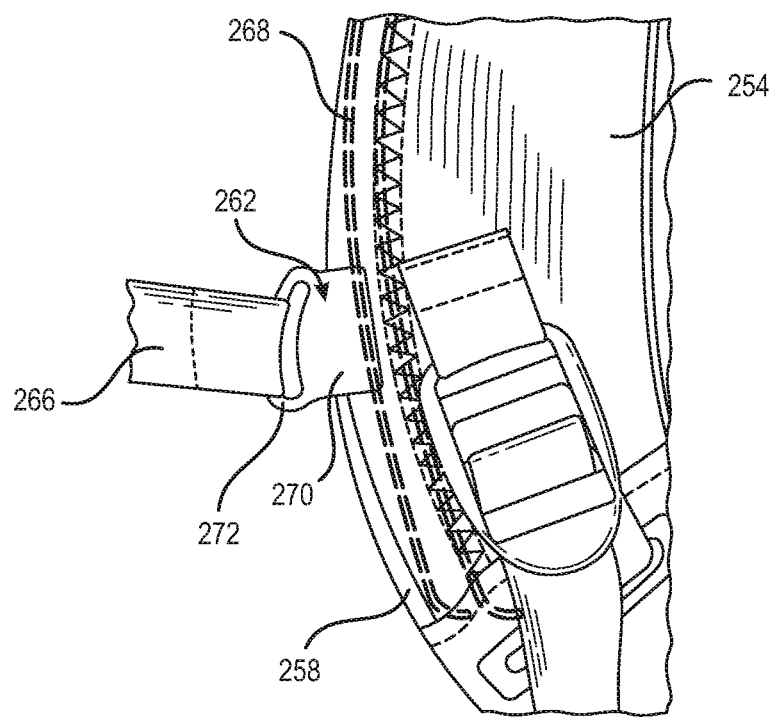
FIG. 9B is a detail view IX B derived from FIG. 9A.

FIG. 9B depicts a detail view of the chest strap 250 usable with an orthosis such as a TLSO attachment having only a posterior component as seen in FIG. 10A below, wherein a chord 268 is located along a softgood of the reinforced edge 258 to retain a shape for the slider 262 to slide along. The slider 262 may include a first end portion contoured to the chord 268, an engager part 270 proximate the first end portion and contoured for convenient gripping by a user, and a second end portion 272 arranged to receive the second strap segment 266. The chest strap 250 can be held in place by the first and second sliders 260, 262, but easily adjusted in height by the user relative to the user's chest.

Figure 9C:
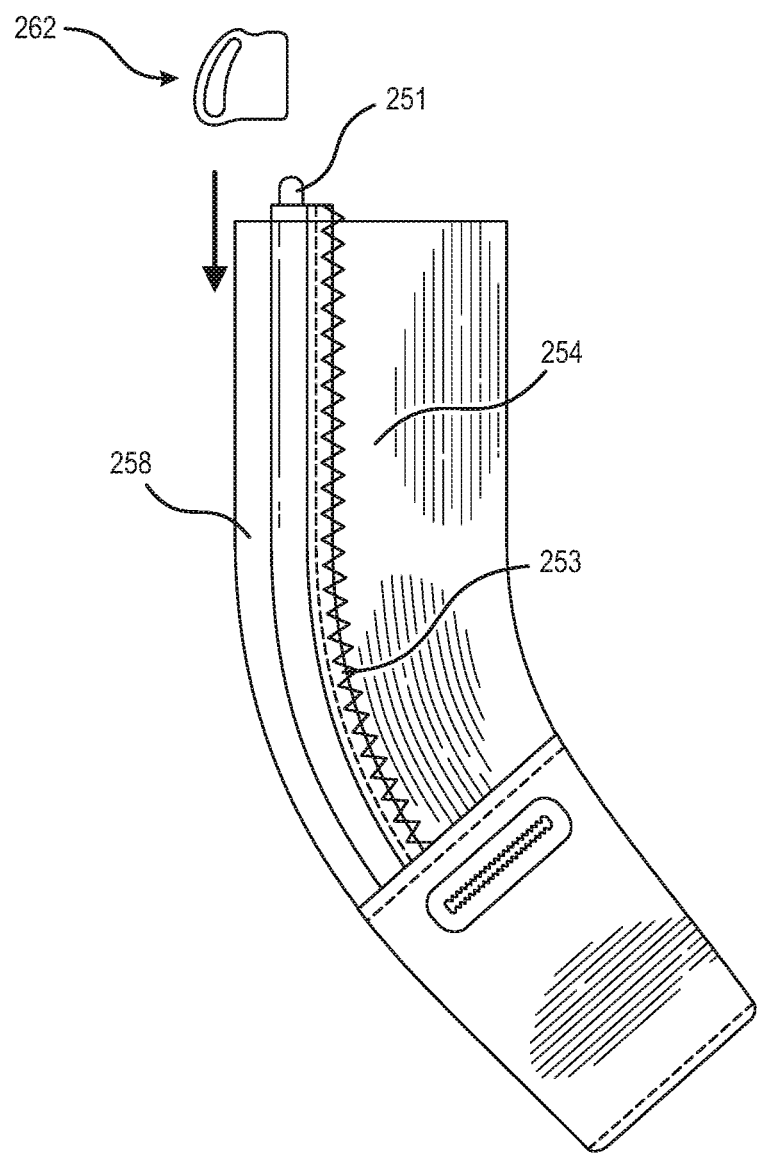
FIG. 9C is a schematic view derived from FIG. 9B.

FIG. 9C depicts in detail view certain elements of the chest strap 250 depicted in FIGS. 9A-B, illustrating in particular the presence and use of a buttress 251 disposed within a pocket defined by each of the first and second straps 252, 254. The buttress 251 may be formed of any suitable material providing added strength and definition to the first and second straps 252, 254, especially as forces are applied to the straps 252, 254 and as the slider 262 translates up and down portions of the first and second straps 252, 254 based on a user's dimensions and needs.

In certain embodiments, the buttress 251 may be an elongate member that provides strength along a substantial length of the first and second straps 252, 254. A material suitable for use as buttress 251 may be polytetrafluoroethylene. A skilled artisan will understand that a variety of other materials, including other polymeric materials, metallic materials, and fabric or synthetic materials, among others, may also be suited for use as buttress 251. The buttress 251 is advantageously retained in place in the embodiment of FIG. 9C by a reinforcement area 253, in which added stitching and stronger stitching patterns are used to retain the buttress 251 in place within the pocket defined by the straps 252, 254, especially as forces are applied to the straps 252, 254.

FIG. 10A illustrates a variation of the TLSO attachment wherein the at least one strap assembly 226 is arranged without the ATE, and is arranged to loop about the shoulders of the user, a sternum strap 228 connects first and second strap segments 234, 236 arranged to extend about a user's shoulders.

FIG. 10B illustrates a variation of the TLSO attachment, wherein the at least one strap assembly 118 is a shoulder strap assembly 118 arranged to connect to the pectoral pads 114 via the fastener 130. In this arrangement, the shoulder strap assembly 118 connects to the ATE 110 and orthopedic device 106 without an axillary strap system.

FIG. 10C illustrates a variation of the TLSO attachment, wherein only an axillary strap system 116 couples to the pectoral pads 114 and the orthopedic device 106, the axillary strap system 116 includes an axillary pad 230 located between the orthopedic device 106 and the pectoral pad 114.

Advantageously, the TLSO attachment of the present disclosure allows for a user to easily select and switch between whichever of the embodiments depicted in FIGS. 10A-C is most appropriate for the user's treatment plan, as each of the TLSO attachment embodiments in FIGS. 10A-C may be broadly compatible and modularly configurable with existing lumbar sacral orthoses, cervical orthoses, and other devices. The TLSO attachment thus provides improved cost, convenience, and effectiveness of treatment for users.

As is readily apparent from the foregoing discussion, it is understood that the size of the orthopedic device and the components thereof can be adjusted so that many different users having different sized joints and body parts may benefit from the present design without the need for custom manufacturing and design. It is also understood that the locations of the various connection points can be alternated from those shown, such that the connection points may be altered from the positions as illustrated herein, as advantageous for users of different dimensions and pathologies.

It is to be understood that not necessarily all objects or advantages may be achieved under any embodiment of the disclosure. For example, those skilled in the art will recognize that the embodiments may be embodied or carried out in a manner that achieves or optimizes one advantage or group of advantages as taught herein without necessarily achieving other objects or advantages as taught or suggested herein.

The skilled artisan will recognize the interchangeability of various disclosed features. Besides the variations described herein, other known equivalents for each feature can be mixed and matched by one of ordinary skill in this art to construct an orthopedic device under principles of the present disclosure.

Although the TLSO attachment is disclosed in certain exemplary embodiments and examples, it therefore will be understood by those skilled in the art that the present disclosure extends beyond the specifically disclosed embodiments to other alternative embodiments and/or uses of the TLSO attachment and obvious modifications and equivalents thereof. It is intended that the present TLSO attachment herein disclosed should not be limited by the particular disclosed embodiments described above.

The invention claimed is:

1. A thoracic lumbar sacral orthosis (TLSO) attachment for configuring a lumbar sacral orthosis (LSO) into a TLSO, the LSO having first and second belt members having hook and loop fastener material and extending from a posterior portion of the LSO, the TLSO attachment comprising:
   an anterior panel;
   an opening exposing a button for selectively engaging an anterior thoracic extension for securing to a shoulder strap system;
   first and second straps extending from upper and lower portions of the anterior panel, respectively;
   first and second side fasteners projecting from the anterior panel; and
   wherein the first strap extends from a center of a tether secured to an uppermost edge of the anterior panel, such that the opening is between the uppermost edge and the tether with the first strap when the first and second straps secure together at a junction over an outer surface of the first belt member;

wherein at least one of the first and second side fasteners secures to an inner surface of the first belt member by engagement of the first and second straps with each other.

2. The thoracic sacral orthosis (TLSO) of claim 1, further comprising a posterior panel arranged to secure to the posterior portion of the LSO.

3. The thoracic lumbar sacral orthosis (TLSO) of claim 2, wherein the posterior panel has a cover arranged to secure over the posterior portion of the LSO.

4. The thoracic lumbar sacral orthosis (TLSO) of claim 3, further comprising a posterior thoracic extension (PTE) attached to a crest of the posterior panel, the PTE defining a shell having an opening extending about a portion of the crest, and at least one end slot for receiving the shoulder strap system.

5. The thoracic lumbar sacral orthosis (TLSO) of claim 4, wherein the PTE further defines a bar adapted for receiving at least one fastener engageable with the posterior panel, the bar being selectively positionable over a height of the crest.

6. The thoracic lumbar orthosis (TLSO) of claim 3, wherein the cover has a central fastener for engaging a surface of the posterior portion of the LSO.

7. The thoracic lumbar sacral orthosis (TLSO) of claim 3, wherein the cover has a first flap defining a portion of the cover arranged to extend over the posterior portion of the LSO, and a second flap having a fastener for engaging the first flap to longitudinally secure the LSO to the posterior panel.

8. The thoracic lumbar sacral orthosis (TLSO) of claim 1, wherein the first side fastener extends through a cut-away in the anterior panel.

9. The thoracic lumbar sacral orthosis (TLSO) of claim 8, further comprising a central fastener located on the anterior panel and arranged to engage the inner surface of the first belt member.

10. The thoracic lumbar sacral orthosis (TLSO) of claim 1, wherein the first and second straps are arranged in length to couple to one another via a coupler at the junction.

11. The thoracic lumbar sacral orthosis (TLSO) of claim 1, wherein the first and second straps are independently attached to the anterior panel separately.

12. A thoracic lumbar sacral orthosis (TLSO) attachment for configuring a lumbar sacral orthosis (LSO) into a TLSO, the LSO having first and second belt members having hook and loop fastener material and extending from a posterior portion of the LSO, the TLSO attachment comprising:
a posterior panel arranged to secure to the posterior portion of the LSO;
a posterior thoracic extension (PTE) attached to the posterior panel;
an anterior panel connecting to at least one of the first and second belt members and comprising an opening exposing a button for selectively engaging an anterior thoracic extension (ATE) for securing to a shoulder strap system;
first and second straps extending from upper and lower portions of the anterior panel, respectively;
wherein the first strap extends from a center of a tether secured to an uppermost edge of the anterior panel, such that the opening is between the uppermost edge and the tether with the first strap when the first and second straps secure together at a junction over an outer surface of the first belt member;
first and second side fasteners projecting from the anterior panel; and
wherein at least one of the first and second side fasteners secures to an inner surface of the first belt member by engagement of the first and second straps with each other;
the anterior thoracic extension (ATE) connecting to the anterior panel;
the shoulder strap system connecting to the PTE and the ATE;
wherein the posterior panel has a cover arranged to secure over the posterior portion of the LSO; and
wherein the cover has a first flap defining a portion of the cover arranged to extend over the posterior portion of the LSO, and a second flap having a fastener for engaging the first flap to longitudinally secure the LSO to the posterior panel.

13. The thoracic lumbar sacral orthosis (TLSO) of claim 12, wherein the PTE defines a shell having an opening extending about a portion of a crest of the posterior panel, and at least one end slot for receiving the shoulder strap system.

14. The thoracic lumbar sacral orthosis (TLSO) of claim 13, wherein the PTE further defines a bar adapted for receiving at least one fastener engageable with the posterior panel, the bar being selectively positionable over a height of the crest.

15. The thoracic lumbar sacral orthosis (TLSO) of claim 12, wherein the first and second straps are arranged in length to couple to one another via a coupler at the junction;
wherein the first and second straps are independently attached to the anterior panel separately.

16. The thoracic lumbar sacral orthosis (TLSO) of claim 12, wherein the first side fastener extends through a cut-away in the anterior panel.

17. A thoracic lumbar sacral orthosis (TLSO) attachment for configuring a lumbar sacral orthosis (LSO) into a TLSO, the LSO having first and second belt members having hook and loop fastener material and extending from a posterior portion of the LSO, the TLSO attachment comprising:
a posterior panel arranged to secure to the posterior portion of the LSO;
a posterior thoracic extension (PTE) attached to a crest of the posterior panel;
an anterior panel connecting to at least one of the first and second belt members and comprising an opening exposing a button for selectively engaging an anterior thoracic extension (ATE) for securing to a shoulder strap system;
first and second straps extending from upper and lower portions of the anterior panel, respectively;
wherein the first strap extends from a center of a tether secured to an uppermost edge of the anterior panel, such that the opening is between the uppermost edge and the tether with the first strap when the first and second straps secure together at a junction over an outer surface of the first belt member;
first and second side fasteners projecting from the anterior panel; and
wherein at least one of the first and second side fasteners secures to an inner surface of the first belt member by engagement of the first and second straps with each other;
the anterior thoracic extension (ATE) connecting to the anterior panel; and
the shoulder strap system connecting to the PTE and the ATE;

the PTE defining a shell having an opening extending about a portion of the crest, and at least one end slot for receiving the shoulder strap system;

wherein the PTE further defines a bar adapted for receiving at least one fastener engageable with the posterior panel, the bar being selectively positionable over a height of the crest.

\* \* \* \* \*